US007910706B2

(12) United States Patent
Tzipori et al.

(10) Patent No.: US 7,910,706 B2
(45) Date of Patent: Mar. 22, 2011

(54) HUMANIZED NEUTRALIZING ANTIBODIES AGAINST HEMOLYTIC UREMIC SYNDROME

(75) Inventors: Saul Tzipori, Shrewsbury, MA (US); Ramaswamy Balakrishnan, Chadds Ford, PA (US); Arthur Donohue-Rolfe, Maynard, MA (US)

(73) Assignee: Trustees of Tufts College, Medford, MA (US)

( * ) Notice: Subject to any disclaimer, the term of this patent is extended or adjusted under 35 U.S.C. 154(b) by 276 days.

(21) Appl. No.: 11/855,699

(22) Filed: Sep. 14, 2007

(65) Prior Publication Data

US 2008/0107651 A1    May 8, 2008

Related U.S. Application Data

(60) Continuation of application No. 10/041,958, filed on Jan. 7, 2002, which is a continuation-in-part of application No. 09/302,125, filed on Apr. 29, 1999, now abandoned, which is a division of application No. 08/749,704, filed on Nov. 15, 1996, now abandoned.

(51) Int. Cl.
*C07K 16/00* (2006.01)
*C12P 21/08* (2006.01)
(52) U.S. Cl. ................... 530/388.15; 530/388.4
(58) Field of Classification Search .................. None
See application file for complete search history.

(56) References Cited

U.S. PATENT DOCUMENTS

| | | | |
|---|---|---|---|
| 4,689,299 | A | 8/1987 | Insel et al. |
| 5,512,282 | A | 4/1996 | Krivan et al. |
| 5,955,293 | A | 9/1999 | Keusch et al. |
| 6,080,400 | A | 6/2000 | Williams et al. |

FOREIGN PATENT DOCUMENTS

| | | |
|---|---|---|
| WO | WO 90/07861 | 7/1990 |
| WO | WO 93/18784 A | 9/1993 |
| WO | WO 98/20903 | 5/1998 |
| WO | WO 99/69629 | 11/1999 |

OTHER PUBLICATIONS

Boerlin, et al., "Associations between virulence factors of Shiga toxin-producing *Escherichia coli* and disease in humans", *J Clin Microbial.*, 37(3):497-503 (1999).
Friedrich, et al., "*Escherichia coli* harboring Shiga toxin 2 gene variants: frequency and association with clinical symptoms", *J Infect Dis.*, 185(1):74-84 (2002).
Hashimoto, et al., "Epidemic of gastrointestinal tract infection including hemorrhagic colitis attributable to Shiga toxin 1-producing *Escherichia coli* O118:H2 at a junior high school in Japan", *Pediatrics*, 103(1):E2 (1999).
Heffernan, Human monoclonal antibody (CP101) for the prevention and treatment of HUS and associated complications caused by Shiga toxin *E. coli*., dated Dec. 2, 2002.
Shoeran, et al, "Stx2-specific human monoclonal antibodies protect mice against lethal infection with *Escherichia coli* expressing Stx2 variants", Infect Immun., 71(6):3125-30 (2003).
37 C.F.R. 1.132 declaration by Dr. John. M. Leong, dated Mar. 27, 2003.
37 C.F.R. 1.132 declaration by Dr. Florian Gunzer, dated Apr. 1, 2003.
37 C.F.R. 1.132 declaration by Dr. Saul Tzipori, dated Apr. 10, 2003.
Chomczynski and Sacchi, "Single-step method of RNA isolation by acid guanidinium thiocyanate-phenol-chloroform extraction," *Anal. Biochem.* 162:156-15-9 (1987).
Donohue-Rolfe et al. "*Escherichia coli* O157:H7 strains that express Shiga toxin (Stx) 2 alone are more neurotropic for gnotobiotic piglets than are isotypes producing only Stx1 or both Stx1 and Stx2," J. Infectious Diseases 181(5):1825-9(2000).
Donohue-Rolfe et al. "Purification of Shiga toxin and Shiga-like toxins I and II by receptor analog affinity chromatography with immobilized P1 glycoprotein and production of cross-reactive monoclonal antibodies" *Infect. Immun*. 57:3888-3893 1989.
Downes, et al., "Affinity purification and characterization of Shiga-like toxin II and production of toxin-specific monoclonal antibodies," *Infect. Immun*.56(8): 1926-1933 (1988).
Edwards, et al, "Vero cell neutralization and mouse protective efficacy of humanized monoclonal antibodies against *Escherichia coli* toxins Stx1 and Stx2," in *Escherichia coli 157:H7 and other Shiga toxin-producing E. coli strains* (Kaper, et al. eds) American Society for Microbiology: Washington D.C., pp. 338-392 (1995).
Engelman, et al., *Human Hybirdemas and Monoclonal Antibodies*, New York: Plenum Press, 23-27 (1985).
Islam, et al."Production and characterization of monoclonal antibodies with therapeutic potential against Shiga toxin," *J. Clin. Lab. Immunol*. 33: 11-16 (1990).
Linton, et al. "Primary antibody-forming cells and secondary B cells are generated from separate precursor cell subpopulations" Cell 59:1049-1059 (1989).
MacLeod, et al. "Immunization of pigs with a purified Shiga-like toxin II variant toxoid," *Vet Microbial*. 29(3-4):309-18 (1991).
Moore, et al., "Production of a Shiga-like cytotoxin by *Campylobacter*," Microbial Pathogenesis 4: 455-462 (1988).
Ol, et al. "Chimeric Antibodies," *Biotechniques* 4(3): 214-226 (1986).
Ostroff, "Infections with *Escherichia coli* O157:H7 in Washington State. The first year of state wide disease surveillance," *JAMA*. 262(3):355-9 (1989).
Ostroff, "Toxin genotypes and plasmid profiles as determinants of systemic sequelae in *Escherichia coli* O157:H7 infections, "*J Infect Dis*. 160(6):994-8(1989).
Perera, et al., "Isolation and characterization of monoclonal antibodies to Shiga-like toxin II of enterohemorrhagic *Escherichia coli* and use of the monoclonal antibodies in a colony enzyme-linked immunosorbent assay," *J. Clin. Microbiol*,. 26(10): 2127-2131 (1988).
Physician's Desk Reference 34th ed. Charles Baker, Jr., pp. 1140-1141 (1980).
Taylor at al. "A transgenic mouse that expresses a diversity of human sequence heavy and light chain immunoglobulins," *Nucl. Acid Res.* 20:6287-6295 (1992).
Tzipori et al. "The role of the eaeA gene in diarrhea and neurological complications in a gnotobiotic piglet model of enterohemorrhagic *Escherichia coli* infection," *Infect. and Immun*. 63:3621-3627, (1995).

Primary Examiner — Mark Navarro
(74) Attorney, Agent, or Firm — Pabst Patent Group LLP

(57) ABSTRACT

Novel human monoclonal antibodies derived from a transgenic mouse are disclosed as well as a process for the preparation of the novel monoclonals and a therapeutic method of treating an individual for hemolytic uremic syndrome or of protecting an individual against hemolytic uremic syndrome by administration of the monoclonals to the individual in need of treatment or protection.

10 Claims, 6 Drawing Sheets

INDIVIDUAL Stx2-SPECIFIC Hu-mAb BINDING PATTERNS

SUMMARY OF Stx2 Hu mAb ACTIVITY
AGAINST CLINICAL Stx2 AND Stx2 VARIANTS

- ● STX 2
- ▲ STX 2a
- ⊠ STX2+STX2a
- ▽ STX 2b
- ○ STX 2c

IN VITRO NEUTRALIZATION OF Stx2 AND Stx2c
(PRODUCED BY CLINICAL STEC ISOLATES)
BY Stx2-SPECIFIC Hu-mAb

5H8 = anti-A+B subunit
6G3 = anti-A+B subunit
2F10 = anti-A subunit
3E9 = anti-A subunit
5C12 = anti-A subunit ns et al. 1986). Although STEC infection occurs mainly in
HUMANIZED NEUTRALIZING ANTIBODIES AGAINST HEMOLYTIC UREMIC SYNDROME

CROSS REFERENCE TO RELATED APPLICATION

This application is a continuation of U.S. Ser. No. 10/041,958 filed Jan. 7, 2002, which is a continuation-in-part of U.S. Ser. No. 09/302,125 filed 29 Apr. 1999, now abandoned, which is a division of U.S. Ser. No. 08/749,704 filed 15 Nov. 1996, now abandoned. The disclosures in the applications listed above is herein incorporated by reference.

STATEMENT REGARDING FEDERALLY SPONSORED RESEARCH

The U.S. government has certain right in this invention by virtue of grants from the National Institutes of Health AI41326 and DK 58993.

FIELD OF THE INVENTION

The present invention relates to new human monoclonal antibodies capable of neutralizing Shiga or Shiga-like toxins which cause hemolytic uremic syndrome in mammals, a process for the preparation of the new human monoclonal antibodies and a method of treating a mammalian subject to prevent the development of hemolytic uremic syndrome in a mammalian subject by administering the monoclonal antibodies to the subject. More particularly the invention relates to human monoclonal antibodies prepared by administering as an antigen to a transgenic mouse having human genes an inactivated Shiga-like toxin to induce an immune response, isolating a splenocyte from the transgenic mouse, fusing the splenocyte to a mouse myeloma cell to form a hybridoma, and screening human monoclonal antibodies produced by the hybridoma for the ability to neutralize Shiga or Shiga-like toxins.

BACKGROUND OF THE INVENTION

Since the first documented outbreaks in 1982, infections from enterohemorrhagic *Escherichia coli* (SHEC), now more commonly referred to as Shiga toxin producing *E. coli* (STEC), have been a major public health concern in the United States and in Europe. It is recognized that the Shiga and Shiga like toxins of *Escherichia coli* 0157:H7 and of other Shiga-producing *E. Coli* strains are pathogenesis factors. In the United States, an estimated 73,000 cases of *E. coli* 0157:H7 and 37,000 non-0157 cases occur annually. Most of the cases occur in children less than 5 years of age. The risk of developing hemolytic uremic syndrome (HUS) following EHEC infection is 3-26%. Usually 5-10% of patients with overt STEC disease develop HUS. There is strong evidence that all postdiarrheal HUS is caused by STEC. HUS is recognized as the major cause of kidney failure in infants and children worldwide. About one-third of HUS patients have abnormal kidney function for many years. About 8% have life long complications such as high blood pressure, seizures, blindness, paralysis . . . (Ostroff, Kobayashi et al. 1989). A small percentage, 0.1-2%, die. Of those who survive HUS, one study showed that half had persistend kidney disease, and 18% progress to end stage renal failure. Mortality in the US from HUS has been estimated to consist of 61 persons. There is no available treatment and antibiotics and anti-diarrheals may exacerbate the problem. Outbreaks of disease have been reported in association with consumption of hamburgers in fast food chains, in nursing homes and in day-care centers. While consumption of contaminated meats, fruits, vegetable and water have led to outbreaks, person to person contact is now recognized as a key mode of transmission (Spika, Parsons et al. 1986). Although STEC infection occurs mainly in children, adults are also susceptible. Worldwide incidence of STEC infection and HUS appears to be similar to that found in the U.S. Since 1996 STEC infection is notifiable in most states. The disease peaks in the warm months but may occur at any time of the year. Bloody diarrhea usually occurs prior to systemic complications which can be either fatal, due to acute renal failure and serious neurological involvement, or lead to permanent kidney damage. The kidney damage and the neurological symptoms which are caused by one of 2 toxins is known as hemolytic uremic syndrome (HUS). In children there is normally a prodromal period of 4 to 7 days between the bloody diarrhea and development of HUS. During this prodromal period an effective preventative treatment, if one was a vailable, might prevent the development of HUS.

Currently there are three accepted characteristics of all STEC strains. First, they all harbor lysogenic lambdoid phages that encode the Shiga toxins. Prophage induction is likely required for toxin production. Shiga and Shiga-like toxins were previously referred to as verotoxins due to their toxicity to vero cells. Shiga-like toxins consist of one enzymatically active A subunit and five B subunits that are responsible for cell binding. The toxins are potent protein synthesis inhibitors and are particularly cytotoxic to both HeLa and Vero cells in culture. Based on antigenic relatedness to Shiga toxin, there are two general classes of Shiga-like toxins. Shiga-like toxin I is neutralized by antibody against Shiga toxin, the toxin produced by Shigella dysenteriae type I strains. Shiga-like toxin II is defined as toxin which is not neutralized by antibody directed against Shiga toxin. By amino acid sequence comparison, SLT-I and SLT-II are 56% homologous. The two toxins have identical sets of glycolipid receptors and an identical mode of action. All EHEC strains isolated to date have been found to produce either one toxin or both. The role of toxin in the pathogenesis of both hemorrhagic colitis and hemolytic uremic syndrome is still not definitive. However, there is strong circumstantial evidence linking SLT II with HUS.

OBJECTS OF THE INVENTION

It is an object of the invention to provide novel human monoclonal antibodies with the ability to neutralize the Shiga toxin or Shiga-like toxin when the monoclonal antibodies are administered to a mammalian subject to treat or prevent toxic uremic syndrome.

It is a further object of the invention to provide novel human monoclonal antibodies having the ability to neutralize the Shiga toxin or Shiga-like toxin upon administration to a mammalian subject, including a human, while at the same time having no adverse side effects on the health of the mammalian subject.

SUMMARY OF THE INVENTION

The invention relates in one aspect to a therapeutic method to treat hemolytic uremic syndrome by administering to an individual a therapeutically effective amount of monoclonal antibody which binds specifically to either Shiga toxin, Shiga like toxin I or Shiga like toxin II. The hemolytic uremic syndrome is typically caused by an enterohemorrhagic *Escherichia coil*. Shiga toxin which is identical to SLT-I is produced by *Shigella* sp.

In another aspect the invention relates to a monoclonal antibody which binds—specifically to Shiga toxin, Shiga like toxin I or Shiga like toxin II. The monoclonal antibody is either a human monoclonal antibody or a chimeric monoclonal antibody. The monoclonal antibody is an immunobuline produced by a hybridoma resulting from the fusion of a mammalian spleen cell that produces the specific antibody and a myeloma cell that can eternalize cell growth. Alternatively the monoclonal antibody can be produced by a trasfectoma resulting from a myeloma transfected with genes encoding antibody production. The species specific properties largely reside in the heavy chain portions. Transgenic mammals can be genetically engineered to produce only human immunoglobulins and can subsequently produce antibodies in response to antigens. Alternatively cells that already produce antibodies that for instance bear murine species specific immunoglobulin heavy chains can be modified through recombinant D N A technology to produce chimeric antibodies that contain heavy human chain regions.

The invention relates in a another aspect to a therapeutic method to treat hemolytic uremic syndrome by administering to an individual a therapeutically effective amount of monospecific polyclonal antibodies which bind specifically to either Shiga toxin, Shiga like toxin I or Shiga like toxin II. The hemolytic uremic syndrome is caused by an enterohemorrhagic *Escherichia coli*, and *Shigella* sp.

In another aspect, the invention relates to monospecific polyclonal antibodies which bind specifically to either Shiga toxin, Shiga like toxin I or Shiga like toxin II. The monospecific polyclonal antibodies are human monospecific antibodies.

DETAILED DESCRIPTION OF THE INVENTION

The present invention is based, in one aspect, on the use of a therapeutic method-to treat-an-individual suffering from hemolytic uremic syndrome (HUS) caused by a virulent strain of an enterohemorraghic *E. coli* (EHEC) or Shiga toxin producing *E. coli* (STEC). The treatment of HUS as disclosed herein involves the use of a monoclonal antibody, a cocktail of monoclonal antibodies or monospecific polyclonal antibodies, which specifically bind either Shiga toxin (ST), Shiga like toxin I (SLT-I) or Shiga like toxin II (SLT-II). Shiga toxin and Shiga like toxin (SLT) are composed of two unique chains, one A subunit and five B subunits, each encoded by toxin genes carried by bacteriophages. The A subunit contains the enzymatic activity, while the five B subunits are responsible for cell binding. HUS is one clinical manifestation among several associated with SLT toxemia and is primarily found to afflict children and the elderly. The most common strain of STEC found associated with outbreaks of HUS in the United States is *Escherichia coli* (*E. coli*) 0157:H7.

Not all monoclonal or polyclonal antibodies against a named antigen are the same. The affinity residing in the antigen binding or Fab portions of the immunoglobulin can vary. Shiga toxins consist of A and B subunits. Antibodies against Shiga toxins can be active against A, B, or various combinations of the A and B subunits. These different antibodies do not necessarily have the same affinities, and thus the same neutralizing abilities. These different antibodies may not all neutralize against various Shiga toxin variants.

The antibodies of the present invention effectively neutralize Shiga toxins that have been shown to cause hemolytic uremic syndrome. Furthermore these antibodies will neutralize representative Shiga toxin variants.

The use of antibodies to protect an individual from ST, SLT-I or SLT-II induced disease is described in more detail in the following section. The experiments described in the following section demonstrated, for example, that antibodies with specificity for SLT could be used to protect a mammal from cerebral hemorrhage and mortality following challenge with a virulent SLT producing bacterial strain. Although the bulk of the in vivo data reported herein were generated in experiments employing piglet indicator assays for protection against SLT-I and/or SLT-II, the fundamental principles are applicable to humans as well. The monoclonal and polyclonal antibodies of the present invention, which bind to either ST, SLT-I or SLT-II, are designed to protect a human individual against the pathologic effects of SLT produced by an EHEC, including HUS. Finally, based on the present disclosure, those of skill in the art will recognize that only routine experimentation will be necessary in order to permit them to rapidly identify monoclonal and polyclonal antibodies for application to the therapeutic treatment of human disease.

The present invention relates in one embodiment to methods for the treatment of an individual suffering from HUS. For example, passive immunization represents one therapeutic approach. Passive immunization can be accomplished using a prophylactically effective amount of a monoclonal antibody, a cocktail of monoclonal antibodies or monospecific polyclonal antibodies. Preferably, such passive immunization is generally accomplished prior to the onset or in the very early stages of the disease.

To treat HUS, a monoclonal antibody, a cocktail of monoclonal antibodies or a monospecific polyclonal antibodies should be given to the affected individual upon detection of the first indications of SLT toxemia. These initial symptoms include the presence of relatively large quantities of blood in diarrhea and bacterial shedding into the feces. If the treatment of HUS S is delayed, the amount of a monoclonal antibody, a cocktail of monoclonal antibodies or monospecific polyclonal antibodies necessary to treat the affected individual will likely be greater than if the treatment regimen had begun early after the first signs of EHEC infection were detected. Treatment may also be warranted if a first individual who has shown no indications of STEC infection is exposed to a second individual who has shown the clinical symptoms associated with an STEC infection. This is especially true in cases where the individual is a child or an elderly person.

The therapeutic amount of antibody given to an individual suffering from HUS will be determined as that amount deemed effective in treating or ameliorating the disease. Normally, a monoclonal antibody, a cocktail of monoclonal antibodies or monospecific polyclonal antibodies will be administered in a pharmaceutically acceptable or compatible carrier. Therefore, the present invention also encompasses pharmaceutical compositions for the treatment of HUS, said compositions comprising a carrier and an effective amount of the monoclonal antibody, cocktail of monoclonal antibodies or monospecific polyclonal antibodies which specifically bind to either ST, SLT-I or SLT-II.

The pharmaceutical compositions are prepared by methods known to one of skill in the art. In general, a monoclonal antibody, a cocktail of monoclonal antibodies or monospecific polyclonal antibodies are admixed with a carrier and other diluents necessary to prepare the pharmaceutical composition, so that it is in a stable and administrable form. Administration of the pharmaceutical composition can be accomplished by several means. These means include, oral, intradermal, subcutaneous, intravenous or intramuscular.

The most efficient means of oral administration will require the pharmaceutical composition to take the form of a tablet or capsule. The tablet or capsule is designed such that dissolution and release of the monoclonal antibody, cocktail of monoclonal antibodies or monospecific polyclonal antibodies will not occur in the stomach. Instead, dissolution will be targeted to occur near to or directly at the site in the intestinal tract where EHREC has colonized. If the aforementioned tablet or capsule does not have these properties, they will need to be given with a solution capable of neutralizing stomach acid. One example of a solution capable of neutralizing stomach acid is sodium bicarbonate, though the present invention is not limited by disclosure of said solution. Application of a monoclonal antibody, a cocktail of monoclonal antibodies or monospecific polyclonal antibodies at the site of colonization will result in both neutralization of SLT at one of the primary sites of production and uptake of the antibodies into the blood stream leading to its dissemination to other sites in the body of the individual where SLT maybe present.

If a capsule or tablet can not be created as a means for the oral ingestion of a monoclonal antibody, a cocktail of monoclonal antibodies or monospecific polyclonal antibodies, a second method of oral administration can be utilized. This method involves a less efficient means of oral administration wherein, a pharmaceutical composition is comprised of a monoclonal antibody, a cocktail of monoclonal antibodies or monospecific polyclonal antibodies admixed with an acid neutralizing solution prior to oral ingestion. The pharmaceutical composition is then orally ingested by the affected individual.

Other methods of administration require pharmaceutical compositions containing carriers that have been documented extensively in the prior art. These alternative methods of administration, intravenous, intramuscular, intradermal and subcutaneous administration can all be accomplished by admixing a monoclonal antibody, a cocktail of monoclonal antibodies or monospecific polyclonal antibodies with a balanced salt solution or its equivalents as the carrier. Selection of a particular balanced salt solution or its equivalents will be well known to one of skill in the art.

Purified SLT antigen is used to immunize animals for the production of monoclonal or polyclonal antibodies which bind specifically to either ST, SLT-I or SLT-II. Production of purified SLT antigen is described in detail in the following section. In general, the method takes advantage of the carbohydrate specificity of the toxin's binding domain. SLT binds specifically to the $P_1$-glycoprotein purified from hydatid cyst fluid. By coupling the $P_1$-glycoprotein to Sepharose 4B, a solid phase system for capturing toxin is generated. To purify SLT, a bacterial lysate containing either SLT-I or SLT-II is applied to a column containing the coupled matrix. Non-specifically and weakly binding material is washed off the column, followed by elution of the SLT with a buffer containing, for example, 4.5M $MgCl_2$. This method has resulted in yields of purified SLT that exceed 80% of the starting material applied to the column. In addition, the purified SLT material has been found to have very high specific activity (cytotoxin activity/mg protein). This scheme is improved over those disclosed in the prior art because it is capable of successfully purifying both SLT-I and SLT-II.

In one aspect of the present invention, human monoclonal and human monospecific polyclonal antibodies are produced by utilizing transgenic mice that are capable of expressing a diversity of human heavy and light chain immunoglobulins. These mice are described-in more detail in the following section. The transgenic mice so used contain the heavy and light chain protein coding regions in an unrearranged configuration according to published procedures (Taylor et al., Nucl. Acid Res. 20:6287-6295 (1992)). To produce human monoclonal or human monospecific polyclonal antibodies with the appropriate specificity, transgenic mice are immunized repeatedly with either purified SLT-I or SLTII. Following immunization of the transgenic mice, spleen cells are isolated and fused with myeloma cells, thus creating human monoclonal antibody cell lines. The specific methods used to produce hybridomas and monospecific polyclonal antibodies have been described in great detail in the prior art and would be known to one of skill in the art.

The most common method used to purify antigen specific polyclonal antibodies from immune serum is immunoaffinity purification on an antigen column. In this method pure antigen, in the present invention either SLT-I or SLT-II, is covalently coupled to a solid support. The immune polyclonal serum is passed through the column, and bound antibody eluted with either a high pH or low pH buffer as disclosed in Antibodies, A Laboratory Manual. Harlow and Lane, Cold Spring Harbor laboratory, 1988.

To determine the neutralizing activity of the ST, SLT-I and SLT-II human monoclonal or human monospecific polyclonal antibodies, tests can be carried out either in vitro in HeLa cells or in vivo in the piglet model (Tzipori et al., infect. and Immun. 63:3621-3627, (1995)). Briefly, gnotobiotic piglets are challenged with E. coli 0157:H7. At various intervals after inoculation, they receive the human monoclonal or human monospecific polyclonal antibodies at various concentrations to establish the optimal therapeutic dose required to protect them from developing severe neurological symptoms and death. After extensive quality, safety, reactogenicity, and efficacy studies in vitro and in various animal systems, the human monoclonal or human monospecific polyclonal antibodies are tested in human volunteers. Following this initial testing, the human monoclonal or human monospecific polyclonal antibodies are included in a pharmaceutical composition as described above to treat individuals suffering from HUS.

In addition, monoclonal antibodies which specifically bind ST, SLT-I or SLT-II can be produced by recombinant DNA methodology. Monoclonal antibody fragments (e.g. Fab fragments) can also be produced in this way. One means of doing this is through the production of a phage display library and the selection of clones with the appropriate specificity (Monoclonal Antibodies from Combinatorial Libraries, Cold Spring Harbor Course, (1993)). This method involves generation of heavy ($V_H$-$C_{H1}$) and light ($V_L$-$C_L$) chain genes in vitro by methods known to one of skill in the art. The library containing recombinantly produced monoclonal antibody (Fab) fragments is cloned into an M13 surface display vector or its equivalent and the resulting M13 phages or their equivalents, displaying anti-ST, anti-SLT-I or SLT-II antibody (Fab) fragments on their surface are screened and selected by bio-panning. The affinities of the monoclonal antibody (Fab) fragments selected by bio-panning can be further improved through DNA mutagenesis by conventional techniques. A large scale preparation is made from a purified single phage plaque, with said preparation used to either prepare phagemid DNA or purify the ST, SLT-I or SLT-II monoclonal antibody (Fab) fragments expressed on the surface of the M13 phage.

In a second aspect, the recombinant DNA methodology is used to produce chimeric monoclonal antibodies which specifically bind either ST, SLT-I or SLT-II. Chimeric monoclonal antibodies are created by excising the heavy (V H) and the light (VL) chain genes from the purified M13 phagemid DNA and cloning them into a human immunoglobulin expression vector. In this vector the human immunoglobulin constant regions are spliced to the 3' end of the monoclonal antibody (Fab) fragment, generating a chimeric monoclonal antibody which in Example 3 of the following section yields a monkey-human chimeric or a mouse chimeric. The immunoglobulin expression vector containing the chimeric monoclonal antibody is transfected by electroporation into a cell line which is defective in Ig chain production.

Transformed cells containing the expression vector encoding the chimeric monoclonal antibody are isolated by conventional means. These cells are then grown in culture and their antibodies purified. Following testing by the methods described above for human monoclonal and monospecific polyclonal antibodies, the chimeric monoclonal antibodies can be used for the therapeutic treatment of individuals suffering from HUS.

The present invention encompasses all monoclonal antibodies that can be generated which specifically bind either ST, SLT-I or SLT-II or their derivatives thereof. This includes those monoclonal antibodies generated with the appropriate specificity by techniques not specifically disclosed in the present Specification. In addition, the present invention encompasses monospecific polyclonal antibodies which specifically bind either ST, SLT-I or SLT-II or their derivatives thereof. Included are those monospecific polyclonal antibodies produced in mice capable of producing human antibody following immunization with either SLT-I or SLT-II.

EXEMPLIFICATION

Example 1

Results

Oral Inoculation of Piglets with *E. coli* o157:H7 Strains

In the present study gnotobiotic piglets were is inoculated within 24 hours after cesarean section with approximately $10^{10}$ viable *E. coli* 0157:H7 organisms and were observed for symptoms over 5 days. Infected piglets normally develop symptoms of diarrhea within 2-3 days after challenge which continue for several days and result in wasting. Histologically, the mucosa of the terminal ileum and the large intestine are severely damaged due to bacterial A-E lesions mediated by the eaeA gene. Challenge of GB piglets with *E. coli* 0157:H7 strains 931, 3100-85, and 933, all SLT-I & II producers, normally lead to diarrhea and wasting, and some 25-30% of them go on to develop ED-like neurological symptoms (Table 1). In contrast, challenge with *E. coli* 0157:H7 strains 86-24 (Table 1) and RCH/86, both SLT-II producers, result in higher incidence of neurological symptoms and death, reaching 100% of animals. In particular, strain RCH/86 was isolated from a fatal case of bloody diarrhea, complicated with HUS and profound neurological symptoms. In piglets, diarrhea and neurological symptoms develop more rapidly with strain 86-24 than with 933.

TABLE 1

Summary of clinical and histological observations in piglets inoculated with two EHEC and 2 control strains.

| Group Number | *E. coli* Strain | Number of animals | Clinical outcome diarrhea | Neurol/ coma/death# | A-E lesions* |
|---|---|---|---|---|---|
| 1. | 86-24 (wild) | 8 | 8 | 8 | + |
| 5. | 933 (wild) | 16 | 16 | 5 | + |
| 6. | *E. coli* HS | 4 | 0 | 0 | − |
| 7. | K12 C600 | 2 | 0 | 0 | − |

Piglets were autopsied within 40 to 72 hours after challenge, with onset of symptoms/death.
*Where (−) indicates no bacterial attaching-effacing (A-E) lesions were observed in any of the animals in this group; (+) indicates extensive lesions were observed in the large intestine and in the terminal ileum in all of them.

The intact gut epithelium forms a formidable barrier which keeps the bulk of SLT in the lumen where it is produced by bacteria in large quantities. Although small amount of SLT-II does get through as is demonstrated clinically in humans and experimentally in piglets, most of it remains in the lumen. A fraction however is taken up and remains bound within the gut mucosa as observed by immunohistochemistry (IHC) in frozen sections. In these sections the amount of mucosa-bound SLT-I is many fold higher than mucosa-bound SLT-II, indicating that SLT-I is "stickier" than SLT-II and could be the reason that it does not readily reach the circulation as does the less sticky SLT-II.

SLT-Specific Murine mAbs

Murine monoclonal antibodies (mAb) were raised against SLT-I and SLT-II. In a first attempt, characterization of 5 mAb cell lines produced against Shiga toxin using immunoprecipitation yielded 3 with the appropriate specificity. One example is 4D3, an IgG mAb specific for the B subunit, which neutralized SLT-I very effectively when preincubated with toxin before addition to the HeLa cells. If toxin was prebound to cells first, the antibody had no significant protective effect. In contrast, the other two mAbs which recognized an epitope on the A subunit, showed less dramatic neutralization when preincubated with toxin before addition to HeLa cells. However, these two mAbs were highly protective when added to cells that were prebound with toxin. All 3 mAbs were IgG1. In a second attempt, mAbs were generated against SLT-II. In this study eight hybridomas were isolated and 4 were characterized. The two B subunit specific mAbs strongly neutralized SLT-II cytotoxicity to HeLa cells. One of these mAbs also cross-reacted with the SLT-I B subunit and was able to neutralize SLT-I cytotoxicity. The two A subunit mAbs had no neutralizing activity and failed to react against the toxin in solution, but reacted with coated toxin on ELISA plates. The two A subunit specific mAbs were IgM and the two B subunit specific mAbs were IgG, one being IgG1 and the other IgG2b.

Challenge and Protection of GB Piglets

Subsequent to challenge with SLT-II producing *E. coli* o157:H7, GB piglets were treated with specific antibodies. Table 2 summarizes the outcome of the challenge-protection experiment, in which 7 of the 8 control animals developed neurological symptoms and died within 72 hours. The animal which did survive, suffered episodes of seizure that lasted several seconds. Of the animals given SLT-II pig immune serum, a total of 3 developed neurological symptoms (1 of 6 from the 12 hour group and 2 of 6 from the 24 hour group). Characteristic discreet hemorrhages in the cerebellum associated with the disease were observed only in the 6 euthanized control piglets. It is not clear why the 3 piglets which developed neurological symptoms despite being given only the immune serum had no such cerebellar lesions. All animals that were challenged had A-E lesions in the colon.

TABLE 2

Survival of GB piglets infected with $10^{10}$ organisms of *E. coli* 0157:H7 strain 86-24, 24 hours after birth. At 6, 12 or 24 after challenge, piglets were injected intraperitoneally (IP) with either 4 ml/kg of SLT-II pig immune serum, or with control pig serum. They were monitored for survival over 72 hours after challenge.

| Serum given* after challenge | Number of Animals | Number of animals Survived 72 hours | Hemorrhages in cerebellum | A-E Lesions |
|---|---|---|---|---|
| No serum given | 2 | 0 | 2 | 2 |
| 12 hr. (control serum) | 6 | 1# | 6 | 6 |
| 6 hr. (SLT serum) | 2 | 2 | 0 | 2 |
| 12 hr. (SLT serum) | 6 | 5 | 0 | 6 |
| 24 hr. (SLT serum) | 6 | 4 | 0 | 6 |

*SLT-II immune serum was produced in a two-months old pig given 4 consecutive intramuscular injections with affinity-purified SLT-II. The control serum was from unimmunized animal.
One surviving piglet displayed occasional fits but survived.

This experiment shows that piglets can be protected from the systemic effect of SLT and death with specific antitoxin neutralizing antibodies, even when given well after the bacterial challenge. In this animal model, the piglets present clinical symptoms approximately 48 hours after challenge, which is a shorter time period than humans. The results that have been presented are significant and suggest that children could likewise be protected against development of renal failure and other systemic complications, if treated early with neutralizing SLT specific antibodies. This is likely to be at the onset of bloody diarrhea or with confirmed infections with SLT producing bacteria. The benefit of antibody administration earlier to sibling of affected individuals, or in an outbreak in a day-care setting, will be much greater. Systemic administration of SLT antibody however did not protect piglets from developing mucosal lesions of A-E and diarrhea. This experiment confirms our hypothesis that treatment with highly specific neutralizing antibodies, even when given after exposure, is very likely to be beneficial. Since the half-life of exogenous Ig in humans is reported to range between 6 and 14 days, probably a single effective dose might be sufficient. Using human mAbs however, multiple injections, if need be, should be reasonably safe. This might occur if plasma exchange is applied.

Materials and Methods
Toxin Purification and Toxoid Production

Hydatid cysts isolated from sheep infected *Echinococcus granulosus* contain material, identified as a glycoprotein, which has Pi blood group reactivity. The $P_1$ glycoprotein's antigenic determinant was subsequently shown to consist of a trisaccharide, Gala-4GalBl-4GlcNAc, identical to the nonreducing end of the $P_1$ glycolipid on human erythrocytes. Shiga toxin, SLT-I and -II bind to terminal Galal-4Gal disaccharide of glycolipids and hence, the P1-glycolipid is a receptor for these toxins. The $P_1$ glycoprotein in hydatid cyst fluid interacts directly with Shiga toxin and inhibits Shiga toxin binding and cytotoxicity to tissue culture cells. By covalently coupling the hydatid cyst glycoprotein to Sepharose 4B a solid phase system for capturing toxin generated. To purify SLT-I, C600(933J) is grown in low syncase medium in the presence of 200 ng/ml of mitomycin C. Mitomycin C induces the 933J bacteriophage carrying the genes for SLT-I. For the purification of SLT-II strain C600(933W) is grown in LB broth in the presence of 200 ng/ml mitomycin C. The toxin from both strains is found predominately in the culture supernatant and the approximate yields are 5 mg/liter for SLT-I and 10 mg/liter for SLT-II. A 70% ammonium sulfate precipitation of the culture supernatant is made and the precipitate dissolved in 10 mM Tris (pH 7.4) and dialyzed against the same buffer. To further purify SLT-I and -II, bacterial lysate is applied to a column containing the coupled matrix. To remove nonspecifically or weakly attached proteins, the column is washed with buffer containing 1 N NaCl and finally toxin is eluted with buffer containing 4.5 M $MgCl_2$. For long term storage the eluted protein is dialyzed extensively against 20 mM ammonium bicarbonate, lyophilized and stored at −70 C. This method results in an increase in specific activity (cytotoxin activity/mg protein) of more than 1000 fold, with yields of toxin greater than 800. In addition to the purification of SLT-I and -II, both the SLT-IIe, the toxin involved in edema disease in pigs and a SLT-II variant from a human isolate have been purified. To immunize either GB or the human monoclonal antibody (HuMAb) mice, toxin will be inactivated by treatment with 4% paraformalaldehyde at 37° C. for two days after which the fixative will be removed by overnight dialysis with PBS. The degree of inactivation will be comparing HeLa cell cytotoxicity of the toxoid to the untreated toxin.

Piglet EHEC Challenge and Protection Model

Twenty-two GB piglets were challenged with a high dose of $10^{10}$ EHEC 0157 to ensure that 100% of animals develop fatal neurological symptoms within 40-72 hours. They were then divided into 5 uneven groups as shown in Table 2. One control group remained untreated, while the second was given 12 hours after bacterial challenge 4 ml/kg IP of serum from normal unimmunized pig. Groups 3-5 were similarly given 4 ml/kg IP of SLT-II specific pig immune serum 6, 12 or 24 hours after challenge, respectively. The SLT-II immune pig serum was collected from a weaned pig which was given 4 consecutive intramuscular injections of affinity-purified SLT-II, and stored in aliquots at −70° C.

Assay of SLT II GB Piglet Immune Sera

Toxin (100 pg/ml) was reincubated for 1 h at room temperature with dilutions of either the pig immune serum or dilutions of mouse ascites fluid containing 4D1 mAb. The pretreated toxin was then added to 96 well tissue culture plates containing HeLa cell monolayers. Each mixture of toxin/antibody concentration was added in triplicate. Following overnight incubation at 37° C. the wells were washed and the remaining cells stained by crystal violet, washed and absorbance read at 595 nm. The medium control is used as the 100% survival level.

Example 2

Construction of Monoclonal Antibodies by Creation of a Phage Display Library The anti SLT-I and SLT-II antibodies are generated by phage surface display technology as follows: In this approach, a library of Heavy ($V_H$-$C_{H1}$) and Light ($V_L$-$C_L$) chain genes are generated in vitro. This library is cloned into an M13 surface display vector (pComb3 or its equivalent) and the resulting M13 phages, displaying anti SLT I and SLT II antibodies on their surface, are screened and selected by bio-panning.

Materials and Methods
Enrichment of Lymphocytes Secreting Anti SLT I and Anti SLT II Antibodies Lymphocytes secreting anti SLT-I and anti SLT-II antibodies are enriched 'according to Linton-et al. (Linton et al., Cell 59:1049-1059 (1989)). Purified lymphocytes are incubated for 45 minutes with 60 nM biotin-SLT-I or biotinSLT-II toxin, washed twice, and then poured onto petridishes coated with streptavidin and blocked with bovine serum albumin, incubated for another 60 minutes at 4° C., and then washed extensively. After the last wash, the petridishes are shaken dry and the bound cells are used for the isolation of total RNA.
Preparation of Total RNA Total RNA is prepared either from purified lymphocytes or from purified and enriched lymphocytes by the modified Chomczynski and Sacchi method (Chomczynski and Sacchi, Anal. Biochem. 162:156-15-9 (1987)). 2 mls RNAzol (Biotecx) per 10-100 mgs of cells is added and the total RNA is isolated according to the manufacturers' recommendation. The total RNA is precipitated with isopropanol and washed with 70% ethanol and resuspended in TE buffer made with DEPC treated water.

Synthesis of cDNA and PCR Amplification of Heavy ($V_H$-$C_{H1}$) and Light ($V_L$-$C_L$) Chains Monkey heavy and light chain cDNAs are synthesized according to Barbas and Burton (Barbas and Burton, Monoclonal Antibodies from Combinatorial Libraries: Cold Spring Harbor Laboratory Course (1993)). 1 µl (10-30 µg) of total RNA is mixed with 1 µl (60 pmoles) of heavy or light chain 3' primer or oligo dT and 5 µl of DEPC treated water. The mixture is heated to 70° C. and cooled slowly. 5 µl of 5× RT buffer, 2 µl of 10 mM dNTP mixture, 0.5 µl of RNasin, 0.5 µl (200 units) of MMLV Reverse Transcriptase and 5 µl of DEPC treated water are added to the sample and incubated at 37° C. for 45 minutes. The resulting cDNA is used in further DNA amplifications using 5' and 3' heavy and light chain amplifiers in the standard PCR protocols. The PCR primers used in the amplification of heavy and light chains have the following restriction sites that allow the double stranded PCR product to be cloned into the pComb3 vector.

5' Heavy chain primer: CTCGAG XhoI
3' Heavy chain primer: ACTAGT SpeI
5' Light chain primer: GAGCTC SadI
3' Light chain primer: TCTAGA XbaI Cloning and Expression of the Synthetic Antibodies (Fab), on the Surface of M 13 Bacteriophage Heavy ($V_H$-$C_{H1}$) and light ($V_L$-$C_L$) chain DNAs are amplified using appropriate PER primers and the cDNA made from the lymphocytes. The amplified double stranded DNA is electrophoretically purified on agarose gels. The purified DNA band (2-5 µg) is cut with suitable restriction enzymes and ligated in pComb3 vector. The ligation mixture is ethanol precipitated and washed with 70% ethanol and air dried. The pellet is dissolved in 10 µl TE. 1-2 µL is used to electroporate XL-1 Blue cells. Transformants are grown at 37° C., in LB amp. After one hour of growth, helper phage VCSM13 is added ($10^{12}$ pfu) and grown for an additional 2 hours. 50 µg/µl of kanamycin is added and the culture is grown o/n at 37° C. M13 phage is prepared from the culture supernatant by standard procedures and is used in biopanning.

Bio-Panning 96 well ELISA plates are coated with 25 gL of either SLT I or SLT II (0.5-0.1 gg/well) in PBS. The plates are incubated at 4° C. for 12 hours. The coating solution is removed and the plates are washed twice with deionized water. After removing the residual water, the plates are blocked with 3% BSA in PBS for 1 hour at 37° C. After removing the 3% BSA solution, 50 µL of phage suspension (approximately ($10^{12}$ pfu) is added to each well and the plates are incubated at 37° C. for 2 hours. At the end, the phage is removed and plates are washed vigorously with TBS/0.5% (TBST). The bound phages are eluted with elution buffer (0.1 M HCl, pH 2.2, adjusted with glycine). This bio-panning is repeated at least three times, with increasing stringency at the wash step and the bound phages are eluted with elution buffer. A large scale phage preparation is made from a purified single phage plaque and the phagemid DNA is prepared. Heavy ($V_H$-$C_{H1}$) and light ($V_L$-$C_L$) chain gene sequences from this plasmid are analyzed. Subsequently, only the variable regions of the heavy ($V_H$) and the light ($V_L$) chain genes are cloned in a human immunoglobulin expression vector. In this vector, the human immunoglobulin constant regions are spliced at the 3' end of the synthetic monkey variable region, generating a synthetic, monkey-human chimeric antibody gene.

Expression and Purification of Recombinant, Monkey-Human Hybrid Anti SLT I and Anti SLT II Antibodies The immunoglobulin expression vector containing the chimeric antibody gene is transfected into mouse myeloma cell line (ATCC CRL 1580), which is defective in IgG chain, by electroporation. After incubation on ice for 10 minutes, the cells are transferred to 20 mls of culture medium and incubated at 37° C. for 48 hours in a $CO_2$ incubator. Cells are plated in a 96 well microtiter plates at density of $2 \times 10^4$. Cells from the master wells secreting the most antibody are subjected to limiting dilution and are plated. Antibodies from the culture supernatant are purified and used in animal studies.

BRIEF DESCRIPTION OF THE DRAWINGS

FIG. 2 is a graph plotting the relative capabilities of the human monoclonal antibodies 2F10, 3E9, 5C12, 5H8, and 6G3 obtained through the use of a transgenic mouse to neutralize the cytotoxicity of each respective Shiga-like Toxin II variants from clinical isolates: STX2, STX2a, STX2b, STX2c, and STX2+Stx2a.

FIG. 5 is a graph comparing the percent in vitro neutralization of Stx2 and Stx2c produced by clinical STEC isolates by Stx2-Specific Human Monoclonal Antibodies 5H8, 6G3, 2F10, 3E9 or 5C12 or control Rabbit polyclonal antibody.

Example 3

Figure 1:
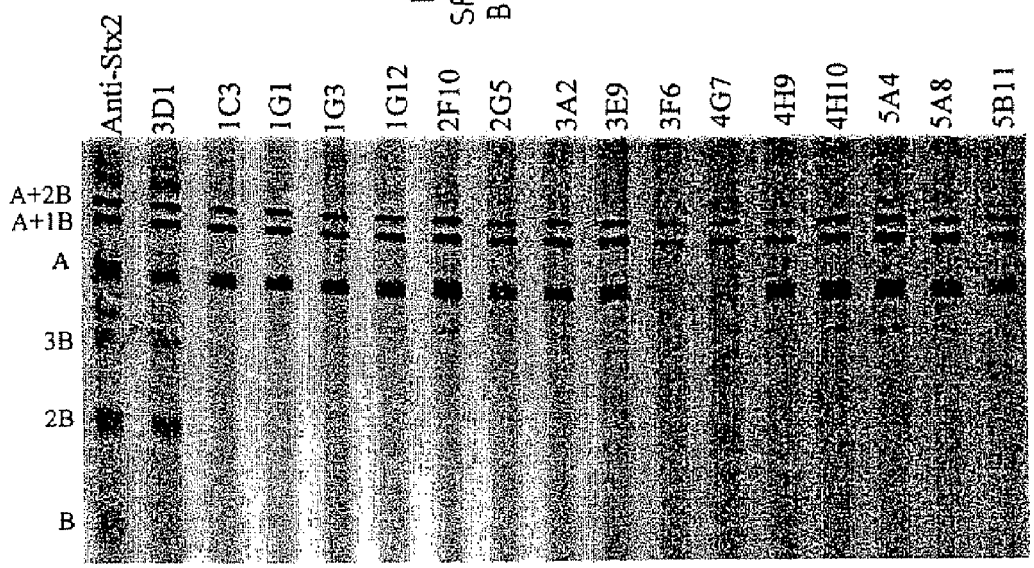
FIG. 1 is a Western Blot Analysis showing the specificity of each of 37 human monoclonal antibodies obtained through the use of a transgenic mouse to bind the A-submit, the B-subunit and the A-B complex subunit of the specific Shiga-like Toxin II Stx2.

Preparation of Specific Human Monoclonal Antibodies Against Shiga-Like Toxin I and Shiga-Like Toxin II Using a Transgenic Mouse and Neutralization of these Toxins Using the New Monoclonal Antibodies Stx2-Specific Hu-mAbs
Methodology Isolation of Stx2. Stx2 was isolated, purified, and quantified as described in Donohue-Rolfe, Acheson, et al. 1989. Briefly, Stx2 was isolated from E. coli strain C600 (933W) which bears the 933WJ bacteriophage that encodes Stx2. E. coli strain C600 (933W) was grown in Modified Syncase Broth at 37° C. with agitation in the presence of 200 ng/ml mitomycin C. Mitomycin C induces the 933J bacteriophage carrying the genes for Stx2. Stx2 in the culture supernatant was precipitated by the addition of 70% ammonium sulfate. The precipitate was dissolved in 10 mM Tris (pH 7.4) and dialyzed against the same buffer. The dialyzed and dissolved precipitate was applied to a Sepharose 4B affinity column containing $P_1$ glycoprotein isolated from *Echinococcus granuloses* hydatid cysts. The $P_1$ glycoprotein contains an antigenic determinant comprised of the trisaccharide, Gal$\alpha$1-4Gal$\beta$1-4GlcNAc, which specifically binds Stx1 and Stx2. The column was washed extensively with 1 M NaCl to remove contaminating proteins. Stx2 is eluted from the column with 4.5 M $MgCl_2$. The eluted Stx2 was then dialyzed extensively against 20 mM ammonium bicarbonate, lyophilized and stored at −80° C.

Preparation of Stx2 Toxoid. Stx2 toxoid was prepared by formalin treatment of purified Stx2. Stx2 was purified from cultures of *E. coli* strain C600 (933W) as described above. Inactivation was confirmed by comparing cytotoxicity of the toxoid versus active Stx2 using HeLa cells.

Hu-MAb™ Mouse. Murine hybridomas producing Stx2-specific Hu-mAbs were generated by fusing spleen cells derived from HuMAb_Mouse™ mice which contain transgenes bearing human immunoglobulin loci with a non-productive murine myeloma. Three distinct sets of HuMAb__Mouse™ mice containing human heavy chain transgenes designated HC2 {Fishwild et al, Nat. Biotechnol. 14, 845-851 1996), HCo7 and HCo12 and the human light chain transgene, HCo5 were used. The heavy chain transgene constructs HC2, HCo7, and HCo12 are comprised of human immunoglobulin heavy chain variable ($V_H$), diversity (D), and joining ($J_H$) segments along with the μ, $\gamma_1 \pm \gamma_3$ constant (C) region exons, the associated switch regions, the $J_H$ intronic enhancer and the rat 3' heavy chain enhancer. The light chain transgene construct KCo5 is comprised of human immunoglobulin light chain variable ($V_k$), joining ($J_k$), and constant ($C_k$) region segments.

To ultimately obtain mice bearing the unrearranged human heavy and light chain immunoglobulin transgenes and unable to produce endogenous murine antibody, two sets of mice were developed. One set of mice lacked the ability to produce endogenous murine antibody. These mice were developed by disrupting the murine kappa light chain locus by injecting mouse embryonic stem cells with a vector containing the neomycin resistance gene. Via homologous recombination the neomycin resistance gene disrupted and replaced both the murine heavy and kappa light chain immunoglobulin gene loci. The embryonic stem cells carrying these targeted disruptions were injected into blastocysts to produce mice bearing deletion of either but not both murine heavy or light chain immunoglobulin loci. Mice bearing deletion of the murine heavy chain immunoglobulin locus were bred to those bearing deletion of the murine light chain immunoglobulin locus to produce mice lacking both murine heavy and kappa light chain immunoglobulin gene loci. A second set of mice bore the human heavy and light chain immunoglobulin transgenes. These mice were developed by injecting mouse embryo pronuclei with one of the human heavy chain immunoglobulin constructs (HC2, HCo7, or HCo12) and the human light chain immunoglobulin construct KCo5 to obtain founder mice bearing both unrearranged human heavy and light chain immunoglobulin gene loci. By breeding mice bearing deletion of both the murine heavy and light chain immunoglobulin gene loci with the mice bearing the human heavy and light chain immunoglobulin gene loci, HuMAb_Mouse™ mice capable of expressing human but not murine antibodies were obtained. In response to immunization, it has been demonstrated that these mice can express 1) antibodies that are entirely comprised of human immunoglobulin structural elements; 2) human antibodies of the IgMκ and IgG1κ±IgG3κ isotypes as a result of class-switching; and 3) human antibodies with evidence of extensive somatic mutation within the human variable regions encoding the expressed antibodies. The ability to express human antibodies which undergo class-switching and somatic mutation in response to a variety of antigens, make these mice a unique means of developing human monoclonal antibodies against a multitude of antigens for a variety of therapeutic applications. HuMAb-Mouse™ mice have only 10-50% of the normal level of B cells and only 20-80% respond to a given antigen with sufficiently high titers to be candidates for fusion to produce monoclonal antibodies, however, this can be overcome by immunizing multiple mice.

Generation of Stx2-Specific Hub-bus Using Hu-MAb™ Mice. Anti-Stx2 Hu-mAbs were generated by immunizing HC2, HCo7, or HCo12 mice with 10-50 μg Stx2 toxoid emulsified in Freund's Complete (initial immunization only) or Incomplete (all subsequent immunizations) Adjuvant i.p. at biweekly intervals a minimum of three times. Serum anti-Stx2 titers were determined by ELISA on microtiter plates coated with 1.5 μg/ml Stx2 and developed with horseradish peroxidase (HRP)-labeled goat anti-human IgG. The spleens of mice with titers 1:800 were fused to the non-productive murine myeloma, P3X63-Ag8.653, by standard methods. Supernatants from hypoxanthine-aminopterin-thymidine-selected hybridomas were successively screened by ELISA on microtiter plates coated with 1.5 μg/ml Stx2 and developed with horseradish peroxidase (HRP)-labeled goat anti-human IgG or HRP-labeled goat anti-human kappa. Stable, positive clones were selected by subcloning twice by limiting dilution and finally by soft-agar cloning.

Hu-mAb-containing ascitic fluid was prepared by injecting hybridoma cells into the peritoneal cavity of pristane-primed ICR-SCID mice. Hu-mAb concentrations in ascitic fluid were determined relative to those of isotype-matched concentration standards by enzyme-linked immunosorbent assay (ELISA).

Isotype Analysis of Stx2-Specific Hu-mAbs. The isotype of each Stx2 Hu-m was determined by ELISA using alkaline phosphatase-labeled anti-human IgM, IgG1, IgG2, IgG3, IgG4, IgA, kappa or lambda.

Analysis of Binding Specificity of Stx2 Hu-mAbs. Stx binding specificity of each Hu-mAb was determined using a sandwich ELISA using murine Stx1 or Stx2-specific mAbs 4D3 or 3D1 to capture Stx1 or Stx2, respectively. Hybridoma culture supernatants containing individual Hu-mAbs were overlaid and developed with alkaline phosphatase-labeled anti-human kappa.

Subunit-Specificity Analysis of Stx2-Specific Hu-mAbs. The subunit specificity of each Stx2 Hu-mAb was determined by Western blot. Stx2 was cross-linked using the homo-bifunctional cross-linking agent, dimethylpimelimidate to create a mixture containing the A subunit bound to one-five B subunits and B subunit alone. The cross-linked Stx2 was electrophoresed by SDS-PAGE on a 15% acrylamide slab gel. Stx2 Hu-mAbs were incubated in the presence of membrane-bound Stx2. Alkaline phosphatase-labeled anti-Fc reagent specific for the anti-Stx2 mAb present, was added to each lane—i.e. goat anti-mouse IgG1 or goat anti-human IgG or IgM. Identification of specific A-B subunit complexes and B subunit multimers was performed as described previously.

In Vitro Neutralization of Stx2. In vitro cytotoxicity assay were used to evaluate the ability of each mAb to neutralize the toxic effects purified Stx2 exerted against HeLa cells. The proportion of surviving cells following exposure to Stx2±Hu-mAb was determined. Stx2-Hu-mAb mixtures were transferred to HeLa cell monolayers and incubated overnight at 37° C. The relative percent neutralization of Stx2 in the presence of Hu-mAb was determined using a standard curve generated based on the effects of Stx2 alone.

Demonstration of Protective Efficacy In Vivo. Two different animal models were used to evaluate the potential efficacy of Stx2-specific Hu-mAbs. A murine toxin neutralization assay was used to assess the relative ability of each Hu-mAb to neutralize the activity of Stx2 in vivo. A gnotobiotic piglet model of E. coli 0157:H7 was used to assess the ability of selected Hu-mAbs to neutralize the activity of Stx2 produced in the gastrointestinal tract during infection and systemically absorbed (a situation which simulates that of human disease).

Using the murine Stx2 neutralization assay, the ability of each Hu-mAb to neutralize the effects of Stx2 in vivo was assessed. Dose-response curves were conducted in groups of five 3-4 week old female Swiss Webster mice to determine the amount of Stx2 required to induce 100% mortality in untreated animals. Hu-mAb efficacy was evaluated by administering 50 µg Stx2 Hu-mAb in 1 ml PBS or 1 ml PBS (control) i.p. to each of 8-10 3-4-week old Swiss Webster mice followed by i.v. administration of 25 ng Stx2, 18 hours later. Mice were observed twice daily for survival.

The gnotobiotic piglet model of E. coli 0157:H7 infection was used to examine the efficacy of selected passively administered Hu-mAbs in preventing the clinical signs and lesions associated with Stx2 during infection. Colostrum-deprived, gnotobiotic piglets were derived by Cesarean section and maintained in sterile microisolators. Within 24 h following derivation, piglets were orally infected with ~1×10$^{10}$ of the Stx2-producing E. coli 0157:H7 strain, 86-24. This high inoculum usually induces neurological signs and lesions associated with Stx2 activity in >85% of untreated piglets within 48-96 h post-infection {Donohue-Rolfe, Kondova, et al, 2000}. Six or twelve hours following infection, piglets were treated with 3 mg Hu-mAb or an equal volume of PBS (control) administered i.p. Piglets were monitored several times each day for development of severe diarrhea or CNS signs (paddling, head-pressing, fore- and hind-limb paresis, seizures, opisthotonous, and/or ventrally fixed eye deviation) associated with Stx2 activity. Piglets which developed such signs or which were alive at the termination of the experiment (6-10 d post-infection) were euthanized and brain tissue (cerebral cortex, cerebellum) obtained and formalin-fixed for histopathological examination for presence of lesions (hemorrhage, edema) associated with Stx2 activity; blood was obtained for determination of serum Hu-mAb concentration. Serum Hu-mAb concentrations were determined relative to those of isotype-matched concentration standards by enzyme-linked immunosorbent assay (ELISA).

Activity of Stx2 Hu-mAbs Against Stx Produced by Clinical Isolates. An in vitro cytotoxicity assay was utilized to examine the relative efficacy of the Stx2-specific Hu-mAbs against Stx2 and Stx2 variants produced by a panel of clinical STEC isolates. Five Stx2-specific Hu-mAbs (2F10, 3E9, 5C12, 5H8, and 6G3) were selected for testing. The efficacy of each Stx2-specific Hu-mAb was tested against thirty-two strains of STEC. Seventeen STEC strains produced Stx2 alone; 7 produced Stx2a alone; 4 produced Stx2+Stx2a; one produced Stx2b; one produced Stx2b+Stx2; and 2 produced Stx2c alone.

Culture supernatants containing the respective Stx was prepared from each of these STEC strains. E. coli 0157:H7 strain 90-2380 which produces Stx2 alone was used as a standard toxin control.

Each assay involved preparing a checkerboard of Stx2-specific Hu-mAb and Stx-containing culture supernatant dilutions. Following incubation, 1.5×10$^4$ VERO cells were added to each well. Following 48 h incubation at 37° C., assay was developed and read. The neutralization index was defined as the $\log_{10}$ of the dilution of toxin neutralized by 1.25 µg/ml Hu-mAb.

Results

Isotype and Subunit Specificity of the Stx2 Hu-mAbs. Thirty-seven stable hybridomas were isolated from transgenic mice bearing the human heavy chain transgenes HC2, HCo7, or HCo12 and the human light chain transgene HCo5. Two of these hybridomas were derived from two mice bearing HC2; 21 were derived from 3 mice bearing HCo7; and 14 were derived from 3 mice bearing HCo12. Thirty-six of the 37 hybridomas isolated secrete IgG1κ Hu-mAbs; one secretes an IgG3κ Hu-mAb (Table 3). As determined by ELISA, each hybridoma secretes Hu-mAb specific for Stx2; no cross-reactivity with Stx1 was observed.

The Stx2 subunit specificity of each fu-mAb was determined by Western blot analysis. Stx2 is comprised of one A subunit of ~32 kD and 5 B subunits each ~7.8 kD. The A versus B subunit-specificity of the anti-Stx2 Hu-mAbs was determined based on binding to covalently cross-linked Stx2 comprised of a mixture of the A subunit bound to zero-five B subunits and B subunit monomers/multimers. Monoclonal antibodies (mAbs) with specificity for the B subunit bind the B subunit monomers/multimers and the A-B complexes; mAbs with specificity for the A subunit bind the A-B complexes but do not bind B subunit monomers/multimers. The relative intensity of binding is determined not only by whether the particular Stx2 entity is recognized by a mAb but also by the percentage of each complex present within the preparation of cross-linked Stx2. Individual Stx2-specific Hu-mAb binding patterns are shown in FIG. 1; the subunit-specificity of each Stx2-specific Hu-mAb is summarized in Table 3. Consistent with either A or B subunit specificity, all 37 Ru-mAbs clearly bound two A-B complexes which based on approximate molecular weights correspond to complexes of the A subunit and 1 or 2 B subunits (A+1B or A+2B). Four Hu-mAbs (3F6, 4G7, 5H8, 6G3) bound entities corresponding to the B subunit monomer (1B), dimer (2B), and trimer (3B), indicating specificity for the B subunit. Although faint, the pattern of 3F6 and 4G7 binding to the 2B and 3B complexes is similar to that of the B subunit-specific murine mAb, 3D1. Both 5H8 and 6G3 however, exhibit different patterns of binding to the B subunit entities-5H8 only binds the 2B complex; 6G3 binds the 1B, 2B, and 3B complexes. These differential patterns of binding are likely indicative of recognition of different epitopes within the B subunit. The lack of binding to B subunit monomer/multimers by the other 33 Hu-mAbs is indicative of specificity for the A subunit. The binding pattern of the A subunit-specific Hu-mAbs is similar, thus differences in epitope specificity cannot be delineated. Consistent with A subunit-specificity, these 33 Hu-mAbs also bind an entity with a molecular weight corresponding to the A subunit monomer (A). Consistent with B subunit specificity, Hu-mAbs 4G7 and 3F6 do not bind the A subunit monomer. However, unexpectedly, the B subunit-specific Hu-mAbs 5H8 and 6G3 and the murine mAb 3D1 do bind the A subunit monomer. This is potentially due to binding an epitope comprised of both A and B subunit moieties.

In vitro and in vivo Neutralization of Stx2. The ability of each Hu-mAb to neutralize the activity of purified Stx2 was studied using both in vitro HeLa cell cytotoxicity assays and an in vivo murine model of Stx2 neutralization (Table 3). Two variations of an in vitro cytotoxicity assay were used to determine the amount of Stx2 neutralized by a given amount of each Hu-mAb. In one assay, Hu-mAb concentration was varied in the presence of a constant amount of Stx2 and the percent of Stx2 neutralized was determined at a single concentration for each Hu-mAb (Table 3). In the second assay, Stx2 concentration was varied in the presence of a constant amount of Hu-mAb and the percent of Stx2 neutralized by each Hu-mAb was determined at a single Stx2 concentration (data not shown). Similar results were obtained with both assays. Using the results of the former in vitro assay, each Hu-mAb was grouped into one of three categories based on relative percent neutralization at a single Hu-mAb and Stx2 quantity (39.1 and 1 ng, respectively) as shown in Table 3. Sixteen Hu-mAbs neutralized $\geq$90% of the Stx2 present (high); 11 neutralized 70-89% of the Stx2 present (medium); and 10 neutralized <70% of the Stx2 present (low).

A murine neutralization assay was used to assess the ability of each Hu-mAb to neutralize Stx2 in vivo. Approximately 18 hours following i.p. administration of 50 µg Hu-mAb, mice were challenged i.v. with 25 ng Stx2. Eight Hu-mAbs (1G3, 2F10, 3E9, 4H9, 5C12, 5H8, 6C3, 6G3; as indicated in Table 3) significantly prolonged average survival to >10 days (experiments were terminated at day 12), relative to the PBS control groups which had average survival values of 2.85-3.9 days. Average in vivo survival did not necessarily correlate with in vitro percent neutralization. Of the 16 Hu-mAbs with high (>90%) in vitro neutralization values, 7 prolonged survival to >10 days; 5 significantly prolonged survival <10 days; and 4 did not significantly prolong survival. Further, one of the 8 Hu-mAbs which prolonged murine survival >10 days had an average in vitro percent neutralization of 81%. Thus, the in vivo murine Stx2 neutralization assay provided a more stringent assessment of the Stx2-neutralizing ability of the Hu-mAbs.

Protection of Gnotobiotic Piglets Infected with *E. coli* 0157:17. Four (2F10, 3E9, 5C12, 5H8) of the eight Hu-mAbs most effective at prolonging murine survival were further studied in a gnotobiotic piglet model of *E. coli* 0157:H7 infection. In this model, 80% of untreated piglets develop neurological signs (Donohue-Rolfe et al, J. Infectious Diseases 181(5): 1825-9 2000). The gnotobiotic piglet model differs substantially from the murine Stx2 neutralization assay-1) Instead of receiving purified Stx2, piglets are infected with an Stx2-producing strain of *E. coli* 0157:H7 and thus develop diarrhea and can become dehydrated similar to humans; and 2) Hu-mAbs are given 6 or 12 h following infection rather than prior to challenge, thereby simulating the situation likely to occur in humans in which Hu-mAbs would be administered following diarrhea development in an effort to prevent HUS. Three parameters were used to assess the effect of Hu-mAb administration relative to untreated PBS control piglets: 1) Prevention of neurological signs (paddling, head-pressing, ataxia, convulsions); 2) Ability to prolong survival; and 3) Prevention of neurological lesions (hemorrhage and edema) within the cerebral cortex and/or cerebellum. Constant monitoring was not possible and as a result piglets occasionally died without the opportunity to observe them during the hours preceding death. For these piglets it is not known whether CNS signs developed and furthermore, examination of brain tissue was not possible. Thus only piglets observed up until the time of death or euthanasia were included in determinations of presence or absence of CNS signs and lesions; however, all piglets which died or were euthanized due to experimental manipulations were included in the survival data. Piglets which died or were euthanized due to unrelated causes (esophageal puncture, extreme weakness, insufficient nourishment and/or severe dehydration) were excluded from the experimental data altogether.

A total of 9 experiments were performed to evaluate the efficacy of administering Hu-mAbs 2F10, 3E9, 5C12, or 5H8 6 or 12 hours following infection (4 representative experiments are shown in Table 4). Nineteen of 21 (90%) control piglets observed immediately prior to death or euthanasia developed neurological signs and 22 of 23 (96%) available for histologic examination had evidence of neurological lesions. In contrast, administration of Hu-mAbs 2F10, 3E9, 5C12, or 5H8 6 or 12 hours post-infection prevented development of neurological signs and lesions in 39 of 42 (93%) treated piglets in these 9 experiments. Two treated piglets which did exhibit convincing neurological signs and lesions had serum Hu-mAb levels <0.01 µg/ml in contrast to the levels of 0.488-15.2 µg/ml in piglets which did not develop neurological signs and/or lesions. Interestingly, one piglet which exhibited both neurological signs and lesions and a second piglet which exhibited only mild neurological lesions, had serum Hu-mAb levels of 2.0 and 8.9 µg/ml, respectively. Although dose response studies have not been performed, and these two treated piglets which exhibited lesions±signs had Hu-mAb levels within the range of those which were protected, this data nonetheless suggests serum Hu-mAb levels of $\geq$0.5 µg/ml are normally sufficient for protection.

In addition to preventing development of fatal CNS signs and lesions, Hu-mAb administration also resulted in a trend toward prolongation of survival. Due to the small sample size present within each experimental group, prolongation of survival of Hu-mAb treated groups versus PBS control groups was not always statistically significant. Nonetheless, the average survival of Hu-mAb groups was greater than control groups in each experiment with the exception of one 3E9 treated group containing a single piglet (data not shown). Significant prolongation of survival was observed at least twice following administration of Hu-mAbs 3E9, 5H8, or 5C12 6 or 12 h post-infection. Comparison of all 44 Hu-mAb treated pigs versus all 31 PBS control pigs indicates Hu-mAb administration does indeed prolong survival ($p \leq 0.0001$).

Efficacy of Stx2-Specific Hu-mAbs Against Clinical Isolates. An in vitro cytotoxicity assay was utilized to determine the relative efficacy of the Stx2-specific Hu-mAbs, 2F10, 3E9, 5C12, 5H8, and 6G3 against Stx2 and/or Stx2 variants (i.e., Stx2a, Stx2, Stx2b) produced by 30 EHEC strains. A neutralization index representing the amount of Stx2 neutralized was determined for each Stx2-specific Hu-mAb-strain combination (Table 5). This neutralization index was plotted as a function of the type of Stx2 produced by the EHEC strain in an effort to compare the efficacy of each Stx2-specific Ru-mAb against the various types of Stx2 (FIG. 2). The neutralization index is a function of both the ability of Hu-mAb to bind the Stx present as well as the amount of Hu-mAb needed to neutralize the cytotoxicity of the Stx present.

Both the Stx2 A-subunit specific (2F10, 3E9, 5C12) and B-subunit specific (5H8, 6G3) Hu-mAbs effectively neutralized the cytotoxic activity of culture supernatants containing Stx2 alone. Hu-mAbs 2F10, 5C12, and 6G3 were most effective against Stx2-containing culture supernatants (neutralization indices >0.5 for all 17 supernatants). In contrast, neutralization indices of <0.5 were observed for Hu-mAbs 3E9 and 5H8 for 1-4 of these Stx2-containing culture supernatants.

Each of the Stx2 A-subunit specific Hu-mAbs 2F10, 3E9, and 5C12 effectively neutralized the cytotoxic activity of 6 of 7 culture supernatants containing Stx2a. Each of these Hu-mAbs was ineffective against the Stx2a produced by EHEC strain 91-8076 (Table 5). Although the toxin profile of each strain was determined by PCR prior to use in this assay, it is possible that the Stx2 produced by EHEC strain 91-8076 was either structurally somewhat different than the Stx2 produced by the other Stx2-producing EHEC strains or that an additional cytotoxic entity, such as Stx1 was indeed produced by this strain. The Stx2 B-subunit specific Hu-mAbs 5H8 and 6G3 exhibited lesser activity against these Stx2a-containing culture supernatants-5H8 exhibited no activity any of the 7 culture supernatants and 6G3 exhibited little or no activity. Given that these B-subunit specific Hu-mAbs were effective against Stx2 but not Stx2a-containing culture supernatants indicates that the structural differences between Stx2 and Stx2a significantly impacted the efficacy of the B-subunit specific Hu-mAbs. Furthermore, the differential activity of these Stx2 B-subunit specific Hu-mAbs against the Stx2-containing culture supernatants suggests differences in epitope specificity between Hu-mAbs 5H8 and 6G3.

Variable efficacy was exhibited against culture supernatants containing Stx2+Stx2a. Both Stx2 A and B subunit specific Hu-mAbs were effective against the Stx2 and Stx2-producing EHEC strains 92-9199, 95-8112, 97-8037. However, only the A-subunit specific Hu-mAbs 2F10 and 3E9 exhibited activity against EHEC strain 97-8075.

The Stx2 A-subunit specific Hu-mAbs, 2F10, 3E9, and 5C12, were effective against the Stx2b-producing strain, 95-0243 and the Stx2c-producing strains E32511 and pJH. In contrast, the Stx2 B-subunit specific Hu-mbs 5H8 and 6G3 were ineffective against these strains. Furthermore, none of the Stx2-specific Hu-mAbs were effective against EHEC strain 95-0459 which produces Stx2+Stx2b.

Overall, based on the spectrum of activity against the Stx2 and Stx2 variants produced by the EHEC strains utilized, the relative efficacy of the Stx2-specific Hu-mAbs is: 2F10>3E9>5C12>6G3>5H8 (FIG. 2). Thus, A-subunit specific Hu-mAbs appear to be superior to B-subunit specific Hu-mAbs. Amongst the A-subunit specific Hu-mAbs, 2F10 3E9, and 5C12, Hu-mAb 5C12 appears to be the most potent—i.e. for those culture supernatants which it exhibits neutralizing ability, the amount of toxin neutralized is greater than when in the presence of Hu-mAbs 2F10 or 3E9.

Factors Affecting Therapeutic Efficacy in Hemolytic Uremic Suyndrome. Numerous epidemiological studies support the observation that Shiga-like toxin II (Stx2) exceeds Shiga like toxin I as a causitive factor in hemolytic uremic syndrome. In this invention selected human monoclonal antibodies were shown to have superior neutralization ability for Stx2 and variants of Stx2 as described in the previous section (Table 5). Furthermore it is noted that the human monoclonal antibodies with superior neutralization ability neutralize the toxin A-subunit only. Note especially the antibodies 5C12, 3E9 and 2F10. In fact simultaneous affinity against the toxin B-subunit may block neutralization in some Stx2 variants. Note the antibodies 5H8 and 6G3. Thus a preferred feature of this invention are the group of human monoclonal antibodies that bind the A-subunit of Stx2 and that neutralization ability against a greater number of Stx2 variants.

Example 4

Stx1-Specific Hu-mAbs

Methodology

Isolation of Stx1. Stx1 was isolated, purified, and quantified as described previously. Briefly, Stx1 was isolated from E. coli strain C600 (933J) which bears the 933J bacteriophage that encodes Stx1. E. coli strain C600 (933J) was grown in Modified Syncase Broth at 37° C. with agitation in the presence of 200 ng/ml mitomycin C. Mitomycin C induces the 933J bacteriophage carrying the genes for Stx1. Stx1 was predominately present in the culture supernatant at a yield of ~5 mg/liter. Stx1 in the culture supernatant was precipitated by the addition of 70% ammonium sulfate. The precipitate is dissolved in 10 mM Tris (pH 7.4) and dialyzed against the same buffer. The dialyzed and dissolved precipitate was applied to a Sepharose 4B affinity column containing $P_1$ glycoprotein isolated from Bichinoccus granuloses hydatid cysts. The $P_1$ glycoprotein contains an antigenic determinant comprised of the trisaccharide, Galα1-4Galβ1-4GlcNAc, which specifically binds Stx1 and Stx2. The column was washed extensively with 1 M NaCl to remove contaminating proteins. Stx1 was eluted from the column with 4.5 M $MgCl_2$. The eluted Stx1 was then dialyzed extensively against 20 mM ammonium bicarbonate, lyophilized and stored at −80° C.

Preparation of Stx1 Toxoid. Stx1 toxoid was prepared by formalin treatment of Stx1. Briefly, 100 µg Stx1 was incubated overnight in 5% formalin and then dialyzed extensively against phosphate buffered saline (PBS). Inactivation was confirmed by comparing cytotoxicity of the toxoid versus active Stx1 using HeLa cells {Donohue-Rolfe, Acheson, et al. Infect. Immun. 57: 3888 to 3893 1989}.

Generation of Stx1-Specific Hu-mAbs Using Hu-MAb™ Mice. Stx1-specific Hu-mAbs were generated by immunizing mice bearing the HCo12 human heavy chain and HCo5 human light chain immunoglobulin construct with 10-50 µg Stx1 toxoid emulsified in Freund's Complete (initial immunization only) or Incomplete (all subsequent immunizations) Adjuvant i.p. at biweekly intervals a minimum of three times. Serum anti-Stx1 titers were determined by ELISA on microtiter plates coated with 1.5 µg/ml Stx1 and developed with horseradish peroxidase (HRP)-labeled goat anti-human IgG. The spleens of mice with titers ≧1:800 were fused to the non-productive murine myeloma, P3X63-Ag8.653, by standard methods. Supernatants from hypoxanthine-aminopterin-thymidine-selected hybridomas were successively screened by ELISA on microtiter plates coated with 1.5 µg/ml Stx1 and developed with horseradish peroxidase (HRP)-labeled goat anti-human IgG or HRP-labeled goat anti-human kappa. Stable, positive clones were selected by subcloning twice by limiting dilution and finally by soft-agar cloning.

Hu-mAb-containing ascitic fluid was prepared by injecting hybridoma cells into the peritoneal cavity of pristane-primed ICR-SCID mice. Hu-mAb concentrations in ascitic fluid were determined relative to those of isotype-matched concentration standards by enzyme-linked immunosorbent assay (ELISA).

Isotype Analysis of Stx1-Specific Hu-mbs. The isotype of each Hu-mAb was determined by ELISA. Briefly, microtiter plates were coated with 1:1000 dilution goat anti-human kappa and blocked with 1% bovine serum albumin in PBS. Hybridoma culture supernatants or ascitic fluid containing individual Hu-mAbs were plated in each of 8 wells. The eight wells were developed with alkaline phosphatase-labeled anti-human IgM, IgG1, IgG2, IgG3, IgG4, IgA, kappa or lambda followed by addition of 1 mg/ml p-nitrophenyl phosphate. Absorbance at 405 nm was determined.

Analysis of Binding Specificity of Stx1-Specific Hu-mAbs. Stx binding specificity of each Hu-mAb was determined using a sandwich ELISA as follows. Microtiter plates coated with 5 µg/ml of the murine Stx1 or Stx2-specific mAbs 4D3 or 3D1 in PBS, were used to capture 1 µg/ml solutions of Stx1 or Stx2, respectively. Hybridoma culture supernatants containing individual Hu-mAbs were plated in duplicate on pairs of plates containing Stx1 or Stx2. Assay was developed with alkaline phosphatase-labeled anti-human kappa followed by addition of 1 mg/ml p-nitrophenyl phosphate. Absorbance at 405 nm was determined.

Subunit-Specificity Analysis of Stx1-Specific Hu-mAbs. The subunit specificity of each Stx1 Hu-mAb was determined by Western blot. Stx1 was cross-linked using the homo-bifunctional cross-linking agent, dimethylpimelimidate to create a mixture containing the A subunit bound to one-five B subunits and B subunit multimers. The cross-linked Stx1 was electrophoresed by SDS-PAGE on a 15% acrylamide slab gel and then electrophoretically transferred to a nylon membrane. Membranes were washed five times with PBS+0.05% TWEEN-20 between each of the following steps. Following electrophoretic transfer, membranes were soaked 1 h in PBS+0.3% TWEEN-20 and then 2 h in PBS+0.05% TWEEN-20+1% BSA. The Surf Blot (model 10.5, Idea Scientific Company, Minneapolis, Minn.) apparatus was used to divide each membrane into 21 discrete lanes. Stx1 Hu-mAbs were incubated at 10 µg/ml in PBS in individual lanes in the presence of membrane-bound Stx1 for 2 h at room temperature versus the previously described Stx1-specific mouse IgG1 mAb 4D3. A 1:1000 dilution of alkaline phosphatase-labeled anti-Fc reagent specific for the anti-Stx1 mAb present, was added to each lane—i.e. goat anti-mouse IgG1 or goat anti-human IgG, or IgM.

In Vitro Neutralization of Stx1. Two variations of an in vitro cytotoxicity assay were used to evaluate the ability of each Stx1-specific Hu-mAb to neutralize the toxic effects of Stx1 exerted against HeLa cells. For each assay, HeLa cells were plated at $2 \times 10^5$/ml in McCoy's 5A medium+10% fetal calf serum and incubated overnight at 37° C. in 5% $CO_2$. Media was removed prior to addition of Stx1-Hu-mAb mixtures. Each assay was performed independently a minimum of 3 times; the results at a selected data point were averaged. Assay I involved examining the effects of limiting Hu-mAb in the presence of Stx1. Each Hu-mAb was serially diluted 1:2 from 12.5 to 0.0061 µg/ml; each dilution was incubated 30 min. at room temperature with 10 ng/ml Stx1. Stx1-Hu-mAb mixtures were transferred to HeLa cell monolayers and incubated overnight at 37° C. The relative percent neutralization of 1 ng Stx1 in the presence of 39.1 ng Hu-mAb was determined using a standard curve generated based on the effects of Stx1 alone (Table 6). Assay II involved examining the effects of Hu-mAb in the presence of limiting Stx1. Stx1 was serially diluted 1:2 from 100 to 0.049 ng/ml; each dilution was incubated 30 min. at room temperature with 1 µg/ml mAb. Stx1-Hu-mAb mixtures were transferred to HeLa cell monolayers and incubated overnight at 37° C. The relative percent neutralization of 0.3125 ng Stx1 in the presence of 100 ng Hu-mAb was determined.

Demonstration of Protective Efficacy In Vivo. A murine Stx1 neutralization assay was used to examine the ability of each Hu-mAb to neutralize the effects of Stx1 In vivo. Dose-response curves were conducted in groups of 3-5 3-4 week old female Swiss Webster mice to determine the amount of Stx1 required to induce 100% mortality in untreated animals (data not shown). Three-four week old female Swiss Webster mice were divided into groups of 6-10. 50 µg Stx2 Hu-mAb in 1 ml PBS or 1 ml PBS (control) was administered i.p. to each of 6-10 3-4-week old Swiss Webster mice followed by i.v. administration of 0.5 µg Stx1 via the lateral tail vein, 18 hours later. Mice were observed twice daily for survival. Experiments were terminated 12 days following Stx1 challenge.

Activity of Stx1 Hu-mAbs Against Stx Produced by Clinical Isolates. An in vitro cytotoxicity assay was utilized to examine the relative is efficacy of the Stx1-specific Hu-mAbs against Stx1 produced by a panel of clinical STEC isolates. Two Stx1-specific Hu-mAbs (15G2 and 5A4) were selected for testing. The efficacy of each Stx1-specific Hu-mAb was tested against ten STEC strains each of which produced Stx1 alone.

Culture supernatants containing Stx1 from each STEC strain were prepared. Each assay involved preparing a checkerboard of Stx1-specific Hu-mAb and Stx1-containing culture supernatant dilutions. Following incubation, 150 µl media containing $1.5 \times 10^4$ VERO cells was added to each well. Following 48 h incubation at 37° C., assay was developed and read. The neutralization index was defined as the $\log_{10}$ of the dilution of toxin neutralized by 1.25 µg/ml Hu-mAb.

Results

Isotype and Subunit Specificity of the Stx1 Hu-mAbs. Eleven stable hybridomas were isolated from transgenic mice bearing the human heavy chain transgenes HCo12 and the human light chain transgene HCo5. Seven of the 11 hybridomas isolated secrete IgMκ Hu-mAbs; 4 secrete IgG1κ Hu-mAbs (Table 6). As determined by ELISA, each hybridoma secretes Hu-mAb specific for Stx1; no cross-reactivity with Stx2 was observed.

The Stx1 subunit specificity of each Hu-mAb was determined by Western blot analysis. Stx1 is comprised of one A subunit of ~32 kD and 5 B subunits each ~7.7 kD {Jackson, Neill, et al. 1987}. The A versus B subunit-specificity of the anti-Stx2 Hu-mAbs was determined based on binding to covalently cross-linked Stx1 comprised of a mixture of the A subunit bound to zero-five B subunits and B subunit monomers/multimers. Monoclonal antibodies (mAbs) with specificity for the B subunit bind the B subunit monomers/multimers and the A-B complexes; mAbs with specificity for the A subunit bind the A-B complexes but do not bind B subunit monomers/multimers. The relative intensity of binding is determined not only by whether the particular Stx1 entity is recognized by a mAb but also by the percentage of each complex present within the preparation of cross-linked Stx1. The subunit-specificity of each Stx1-specific Hu-mAb is summarized in Table 6. Consistent with either A or B subunit specificity, all 11 Stx1 Hu-mAbs clearly bound an A-B complex which based on approximate molecular weight corresponds to a complex of the A subunit and one B subunit (A+1B). Ten of the Stx1 Hu-mAbs (1B10, 2D9, 5A4, 8A5, 10F4, 13F1, 14C9, 14H3, 15G2, 1S59) bound entities corresponding to the B subunit monomer (1B) and trimer (3B), indicating specificity for the B subunit. The lack of binding to B subunit monomer/multimers by Stx1 Hu-mAb 7E12 is indicative of specificity for the A subunit. Unexpectedly, the B subunit-specific Stx1 Hu-mAbs also bind the A subunit monomer. This is potentially due to binding an epitope comprised of both A and B subunit moieties.

In vitro and in vivo Neutralization of Stx1. The ability of each Stx1 Hu-mAb to neutralize the activity of purified Stx1 was studied using both in vitro HeLa cell cytotoxicity assays and an in vivo murine model of Stx1 neutralization (Table 6). Using the in vitro cytotoxicity assay, the Stx1 Hu-mAb concentration was varied in the presence of a constant amount of Stx1 and the percent of Stx1 neutralized was determined at a single concentration for each Hu-mAb (Table 6).

A murine neutralization assay was used to assess the ability of each Hu-mAb to neutralize Stx1 in vivo. Approximately 18 hours following i.p. administration of 50 μg Hu-mAb, mice were challenged i.v. with 0.5 μg Stx1. The results of both the in vitro and in vivo Stx1 neutralization assays were used to group the Stx1 Hu-mAbs into two categories-those which were highly neutralizing (≧85% neutralization in vitro and prolonged average survival to >10 days; and those which were moderately neutralizing (84-55% neutralization in vivo and prolonged average survival <10 days). Stx1 Hu-mAbs 2D9, 5A4, 10F4, 15G2, 15G9 were found to be highly neutralizing (Table 6, upper panel); whereas, Stx1 Hu-mAbs 1B10, 7E12, 8A5, 14C9, and 14H3 were found to be only moderately neutralizing (Table 6, lower panel). Unlike the Stx2 Hu-mAbs, the neutralization observed in vitro and in vivo for the Stx1 Hu-mAbs, correlated.

Figure 3:
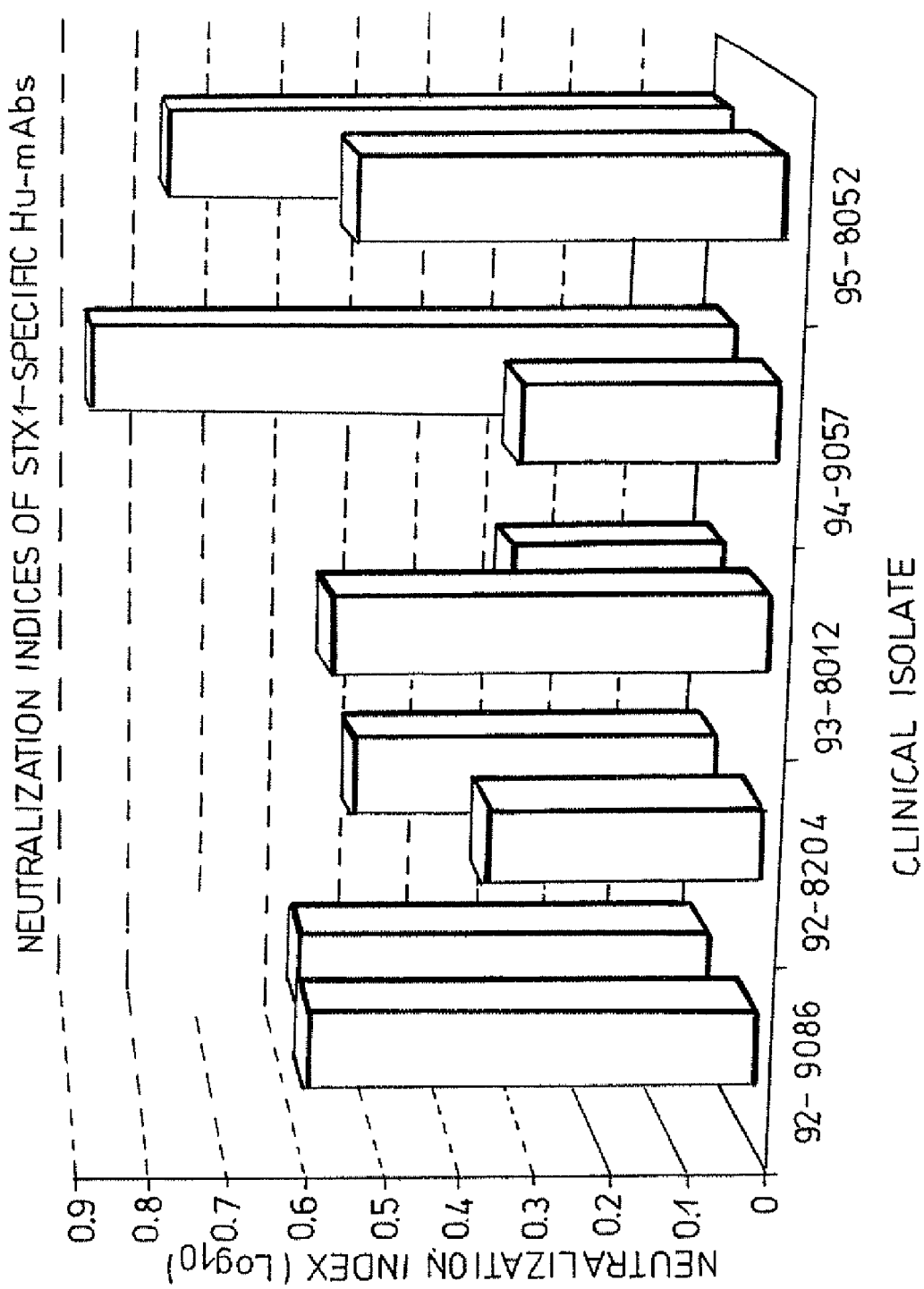
FIG. 3 is a graph showing the relative capabilities of the human monoclonal antibodies 5A4 and 15G2 obtained through the use of a transgenic mouse to neutralize each respective Shiga-like Toxin I obtained from the Stx1 clinical isolates from STEC strains 92-9086, 92-8204, 93-8012, 94-9057, and 95-9052.
Figure 4:
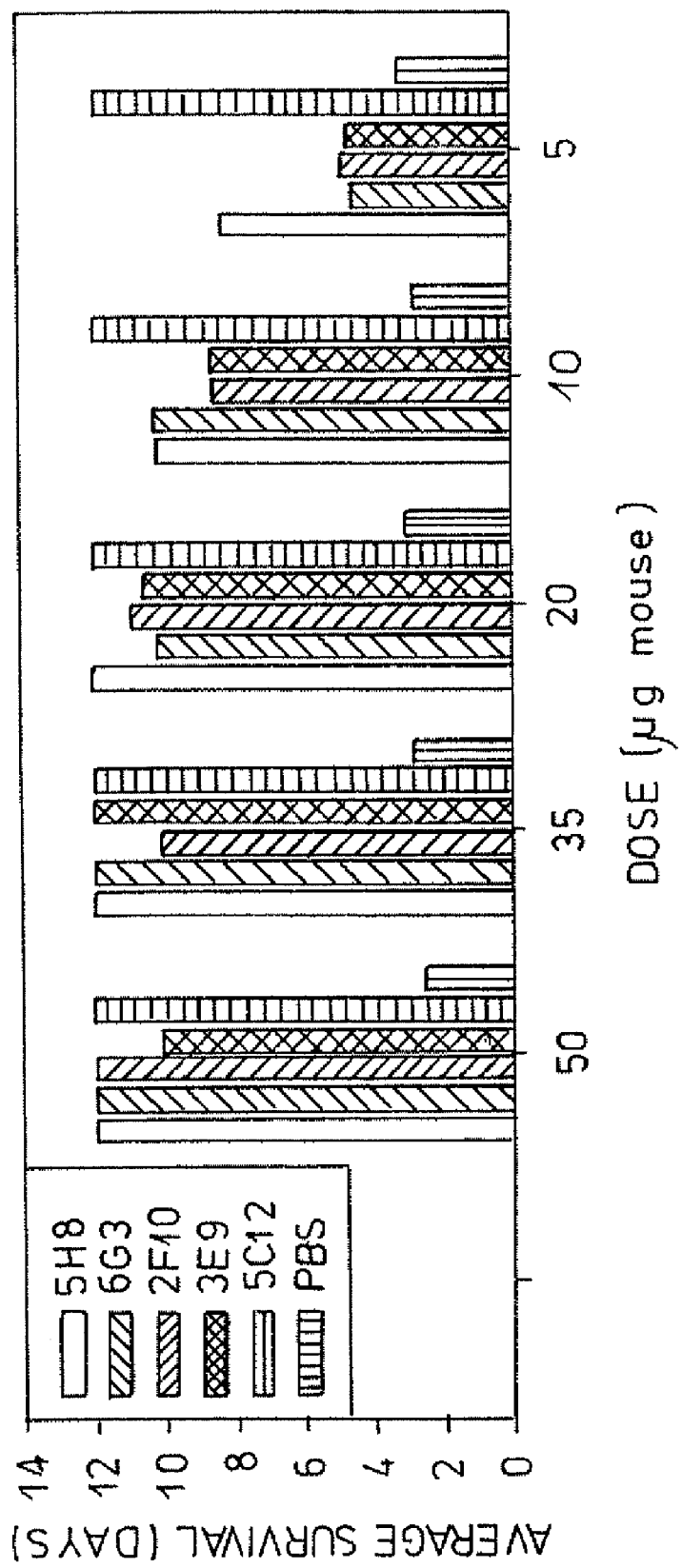
FIG. 4 is a graph comparing the average survival times for mice given 5, 10, 20, 35, or 50 µg of Stx2-specific Hu-mAbs followed 18 hours later with 25 ng Stx2.
Figure 6:
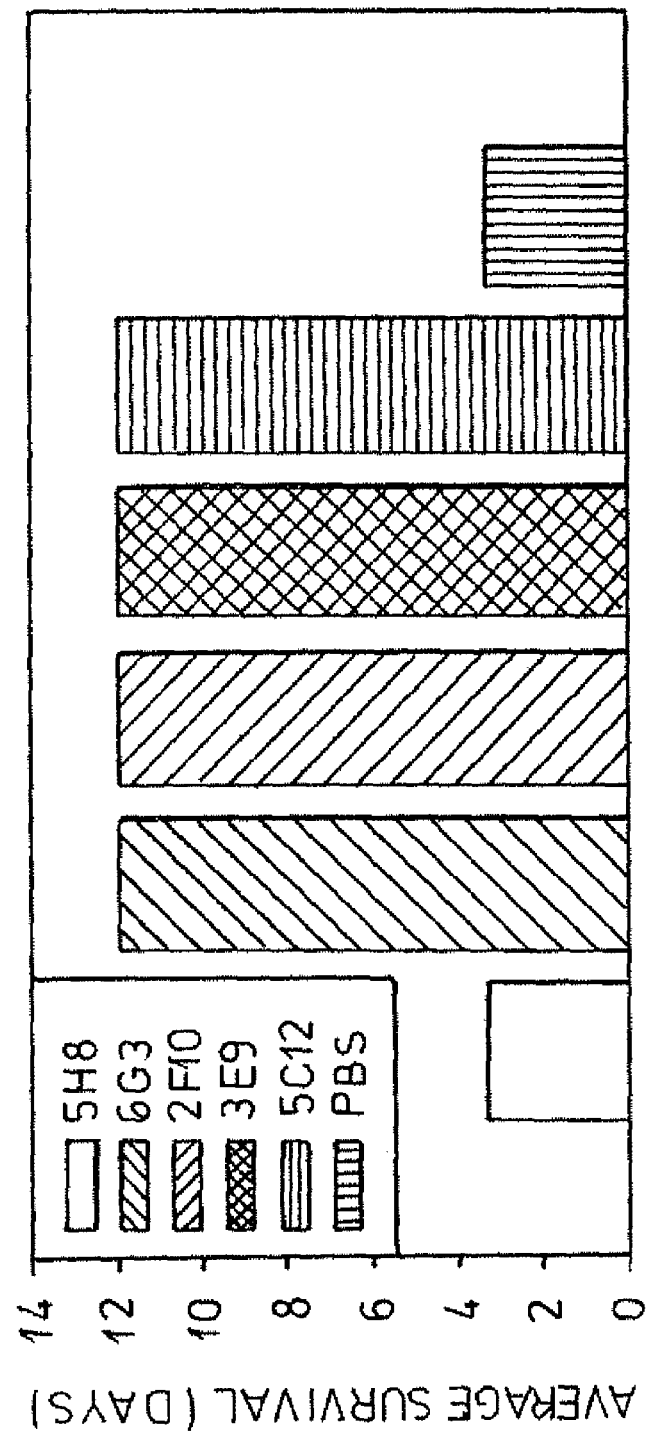
FIG. 6 is a graph comparing the average survival time of mice given 30 µg of Stx2-Specific Human Monoclonal Antibodies 5H8, 6G3, 2F10, 3E9 or 5C12 or control PBS followed 18 hours later with 25 ng Stx2c containing culture supernatant obtained from Stx2c producing E. coli isolate (95-8061).

In Vitro Efficacy of Stx1-Specific Hu-mAbs Against Clinical Isolates. An in vitro cytotoxicity assay was utilized to determine the relative efficacy of the Stx1-specific Hu-mAbs, 15G2 and 5A4 against 5 Stx1-producing STEC strains. A neutralization index representing the amount of Stx1 neutralized was determined for each Stx1-specific Hu-mAb-strain combination. Stx1-specific Hu-mAbs, 15G2 and 5A4, were effective at neutralizing the Stx1 produced by each of the 5 clinical isolates tested (FIG. 3). This result is in concordance with the fact that Stx1 is structurally homogeneous.

DEPOSIT OF HUMAN MONOCLONAL ANTIBODIES

Tufts 5C12 human monoclonal antibody to Shiga toxin was deposited by Tufts University on Dec. 20, 2001 under the terms of the Budapest Treaty on the International Recognition of the Deposit of Microorganisms for the purposes of Patent Procedure with the American Type Culture Collection ("ATCC"), Manassas, Va. 20110-2209, United States, Patent Deposit Designation PTA-3944. The deposited antibody will be maintained for at least 30 years from the date of deposit or five years from the most recent request for a sample, whichever is longer. The deposited antibody will be made available upon written request to the ATCC. All restrictions imposed by the depositor on the availability to the public of the deposited material will be irrevocably removed upon the granting of the patent.

TABLE 3

Summary of the Stx2 Hu-mAb Isotype, Epitope Specificity, in vitro and in vivo Stx2 Neutralization.[a]

| mAb | Isotype | Stx2 Subunit Specificity | HeLa Cell Cytotoxicity Assay (% Neutralization of Stx2 ± S.D.)[b] | Murine Survival[c] Average ± S.D. (Days) | p-value |
|---|---|---|---|---|---|
| 1G1 | IgG1 | A | 92.0 ± 7.2 | 3.35 ± 0.412 | 0.0101[e] |
| 1G3 | IgG1 | A | 98.6 ± 1.2 | 10.5 ± 3.16 | 0.001[d] |
| 2F10 | IgG1 | A | 99.6 ± 0.3 | 12.0 ± 0 | 0.001[d] |
| 3E9 | IgG1 | A | 99.2 ± 0.7 | 12.0 ± 0 | 0.001[d] |
| 4G7 | IgG3 | B | 99.3 ± 0.2 | 6.1 ± 4.095 | 0.0035[e] |
| 4H9 | IgG1 | A | 94.5 ± 3.1 | 10.25 ± 3.691 | 0.0018[f] |
| 5A4 | IgG1 | A | 97.7 ± 2.1 | 8.7 ± 4.27 | 0.0011[d] |
| 5C12 | IgG1 | A | 99.7 ± 0.3 | 12.0 ± 0 | 0.001[e] |
| 5H8 | IgG1 | A + B | 96.0 ± 2.2 | 11.2 ± 2.53 | 0.001[d] |
| 6G3 | IgG1 | A + B | 98.4 ± 2.1 | 12.0 ± 0 | 0.001[e] |
| 6H5 | IgG1 | A | 94.7 ± 2.2 | 3.1 ± 0.81 | 0.4680[d] |
| 6H7 | IgG1 | A | 90.4 ± 3.8 | 2.7 ± 0.35 | 0.0071[d] |
| 7C4 | IgG1 | A | 99.5 ± 0.2 | 7.65 ± 4.59 | 0.0156[d] |
| 9F9 | IgG1 | A | 95.7 ± 1.7 | 5.38 ± 4.095 | 0.2190[e] |
| 9H9 | IgG1 | A | 94.3 ± 1.1 | 4.35 ± 2.87 | 0.3737[d] |
| 14C12 | IgG1 | A | 97.9 ± 2.4 | 4.3 ± 2.72 | 0.1579[d] |
| 1C3 | IgG1 | A | 86.2 ± 4.5 | 2.9 ± 0.61 | 0.2380[d] |
| 2G5 | IgG1 | A | 87.2 ± 11.7 | 5.1 ± 3.76 | 0.4047[d] |
| 4H10 | IgG1 | A | 73.7 ± 12.4 | 8.5 ± 4.52 | 0.0012[e] |
| 5A8 | IgG1 | A | 82.2 ± 6.2 | 3.7 ± 2.96 | 0.3495[d] |
| 5B11 | IgG1 | A | 81.3 ± 1.5 | 3.3 ± 0.89 | 0.9004[d] |
| 5E12 | IgG1 | A | 84.2 ± 2.4 | 4.0 ± 2.88 | 0.7591[d] |
| 6C3 | IgG1 | A | 81.3 ± 14.2 | 12.0 ± 0 | 0.001[e] |
| 6D8 | IgG1 | A | 78.7 ± 12.1 | 3.2 ± 0.363 | 0.0254[e] |
| 6E6 | IgG1 | A | 86.7 ± 4.1 | 2.8 ± 0.63 | 0.1989[d] |
| 7G2 | IgG1 | A | 75.0 ± 11.5 | 3.2 ± 0.350 | 1.000[f] |
| 1G12 | IgG1 | A | 46.4 ± 22.0 | 3.1 ± 0.211 | 0.0292[e] |
| 3A2 | IgG1 | A | 47.3 ± 41.5 | 3.85 ± 2.868 | 0.5983[f] |
| 3F6 | IgG1 | B | 22.0 ± 38.1 | 2.8 ± 0.258 | 0.1888[e] |
| 5F2 | IgG1 | A | 62.7 ± 0.6 | 4.15 ± 2.78 | 0.0129[e] |
| 6B7 | IgG1 | A | 60.5 ± 52.6 | 3.45 ± 0.956 | 0.0227[e] |
| 6C12 | IgG1 | A | 51.4 ± 40.6 | 3.7 ± 0.63 | 0.0012[d] |
| 7B3 | IgG1 | A | 69.2 ± 11.1 | 3.1 ± 0.70 | 0.4664[d] |
| 7F2 | IgG1 | A | 64.3 ± 28.1 | 5.95 ± 4.186 | 0.0047[e] |

TABLE 3-continued

Summary of the Stx2 Hu-mAb Isotype, Epitope Specificity, in vitro and in vivo Stx2 Neutralization.[a]

| mAb | Isotype | Stx2 Subunit Specificity | HeLa Cell Cytotoxicity Assay (% Neutralization of Stx2 ± S.D.)[b] | Murine Survival[c] Average ± S.D. (Days) | p-value |
|---|---|---|---|---|---|
| 10E9 | IgG1 | A | 62.0 ± 15.1 | 2.75 ± 0.354 | 0.0230[e] |
| 11B12 | IgG1 | A | 52.0 ± 45.0 | 4.15 ± 2.769 | 0.0041[e] |

[a]Hu-mAbs have been sorted into three groups based on average percent neutralization of Stx2 in vitro. Within table, groups are divided using double lines. Upper, middle, and lower groups include Hu-mAbs with in vitro percent neutralization values of ≧90%, 70-89%, and <70%, respectively. Each percent neutralization represents the average of 3 values obtained from independent experiments.
[b]Average percent neutralization of 1 ng Stx2 in presence of 39.1 ng Hu-mAb.
[c]Experiments were terminated on day 12; n = 8-10 mice per group. Hu-mAbs which prolonged survival an average of >10 days are indicated in bold type.
[d]Survival of PBS control was 3.3 ± 0.35 days.
[e]Survival of PBS control was 2.85 ± 0.24 days.
[f]Survival of PBS control was 3.9 ± 2.85 days.

TABLE 4

Effect of Stx2 Hu-mAb Administration on Gnotobiotic Piglets Infected with Strain 86-24 *E. coli* O157:H7

| Exper. #[a] | Treatment Group | Hu-mAb Dose (mg) | Timing (Hours Post-Infection) | CNS Signs[b] | CNS Lesions[c] | Survival[d] Average ± S.D. (Days) | p-value | n | Average Serum Human IgG Level ± S.D. (μg/ml) |
|---|---|---|---|---|---|---|---|---|---|
| 104 | PBS | 0 | 6 | 3/4 | 3/4 | 3.8 ± 2.08[f] | — | 5 | ND[g] |
|  | 3E9 | 3 | 6 | 0/5 | 0/5 | 6.7 ± 0.67[f] | 0.044 | 5 | 4.91 ± 2.8 |
|  | 5H8 | 3 | 6 | 0/2 | 0/2 | 7.0 ± 0[f] | 0.083 | 2 | 3.84 ± 0 |
| 117 | PBS | 0 | 12 | 2/2 | 2/3 | 6.67 ± 1.53 | — | 3 | ND[g] |
|  | 3E9 | 3 | 12 | 0/4 | 0/4 | 10.0 ± 0[f] | 0.0157 | 4 | 5.16 ± 2.8 |
|  | 5H8 | 3 | 12 | 0/3 | 0/3 | 10.0 ± 0[f] | 0.0287 | 3 | 2.82 ± 0.4 |
| 115 | PBS | 0 | 12 | 3/3 | 3/3 | 3.83 ± 1.04 | — | 3 | ND[g] |
|  | 2F10 | 3 | 12 | 0/3 | 1/4[e] | 6.0 ± 1.35[f] | 0.0683 | 4 | 8.85 ± 2.1 |
| 128 | PBS | 0 | 12 | 5/5 | 5/5 | 3.2 ± 0.98 | — | 5 | ND |
|  | 5C12 | 3 | 12 | 0/4 | 0/4 | 8.6 ± 3.13 | 0.005 | 5 | 4.81 ± 6.97 |

[a]Experiments 104, 115, 117, and 128 were terminated on days 7, 8, 10, and 10, respectively.
[b]CNS signs included paddling, head-pressing, seizures, opisthotonous, and/or ventrally fixed eye deviation. Only piglets observed immediately prior to death or euthanasia were included in observations.
[c]CNS lesions included hemorrhage and edema present within histopathological sections of the cerebrum and/or cerebellum.
[d]Average survival of gnotobiotic piglets following administration of 3 mg Hu-mAb 6 or 12 hours following oral infection with *E. coli* O157:H7 strain 86-24. All piglets which died or were euthanized due to experimental manipulations were included in the survival data. p-values were calculated for the comparison of average survival of PBS control groups and Hu-mAb treated groups by parametric (log-rank) and non-parametric (Wilcoxon) analyses. Comparable p-values were obtained with both analyses. The table shows p-values obtained by log-rank analysis.
[e]The lesions present within the CNS tissue of one piglet within this group were very mild and thus not conclusive. Nonetheless, the piglet was included with those that had definite lesions.
[f]Average includes censored data points, i.e. animals alive at the termination of the experiment. Analysis accounted for censored observations (animals alive at termination of experiment) and thus estimate of the mean in these groups is biased against prolongation of survival.
[g]ND = not detectable.
[h]NA = not available.

TABLE 5

Neutralization Indices of of Stx2-Specific Hu-mAbs[a].

| EHEC Strain | Toxin Profile of EHEC Strain | 2F10 (anti A) | 3E9 (anti A) | 5C12 (anti A) | 5H8 (anti A + B) | 6G3 (anti A + B) |
|---|---|---|---|---|---|---|
| 91-8000 | Stx2 | 0.68 | 0.45 | 1.16 | 0.35 | 0.56 |
| 91-8069 | Stx2 | 0.9 | 0.93 | 1.52 | 0.85 | 1.1 |
| 92-9035 | Stx2 | 0.95 | 0.66 | 1.19 | 0.43 | 0.87 |
| 93-8059 | Stx2 | 1.15 | 0.72 | 1.09 | 1.37 | 1.05 |
| 93-8073 | Stx2 | 1.0 | 0.82 | 1.43 | 0.86 | 0.95 |
| 93-8094 | Stx2 | 0.64 | 0.6 | 1.4 | 0.9 | 0.99 |
| 93-8127 | Stx2 | 0.77 | 0.88 | 1.1 | 0.68 | 1.25 |
| 93-8132 | Stx2 | 0.78 | 0.51 | 1.15 | 0.94 | 1.05 |
| 93-8176 | Stx2 | 0.88 | 0.71 | 0.9 | 0.56 | 1.02 |
| 94-9004 | Stx2 | 1.33 | 0.95 | 1.42 | 0.77 | 1.13 |

TABLE 5-continued

Neutralization Indices of of Stx2-Specific Hu-mAbs[a].

| EHEC Strain | Toxin Profile of EHEC Strain | Stx2-Specific Hu-mAb | | | | |
|---|---|---|---|---|---|---|
| | | 2F10 (anti A) | 3E9 (anti A) | 5C12 (anti A) | 5H8 (anti A + B) | 6G3 (anti A + B) |
| 94-9028 | Stx2 | 1.03 | 0.66 | 1.12 | 0.62 | 0.99 |
| 94-9038 | Stx2 | 0.81 | 0.77 | 1.13 | 0.45 | 1.29 |
| 94-9050 | Stx2 | 1.04 | 0.62 | 0.77 | 0.81 | 1.33 |
| 94-9059[b] | Stx2 | 0.77 | 1.06 | 1.2 | 0.53 | 1.06 |
| 95-8049 | Stx2 | 0.66 | 0.6 | 1.16 | 0.75 | 0.93 |
| 95-8080 | Stx2 | 1.1 | 0.66 | 1.32 | 0.72 | 0.75 |
| 96-9102 | Stx2 | 0.76 | 0.64 | 1.12 | 0.44 | 1.03 |
| 91-8076[b] | Stx2a | 0 | 0 | 0 | 0 | 0.13 |
| 91-8099 | Stx2a | 1.22 | 0.74 | 1.26 | 0 | 0 |
| 92-9140 | Stx2a | 0.96 | 0.61 | 1.3 | 0 | 0 |
| 93-8021 | Stx2a | 1.14 | 0.4 | 0.93 | 0 | 0.38 |
| 93-8053 | Stx2a | 1.07 | 0.15 | 0.35 | 0 | 0.32 |
| 94-8055 | Stx2a | 0.9 | 0.56 | 1.02 | 0 | 0 |
| 95-8061 | Stx2a | 0.76 | 0.62 | 0.4 | 0 | 0.19 |
| 92-9199 | Stx2 + Stx2a | 0.6 | 0.8 | 1.0 | 0.5 | 0.93 |
| 95-8112 | Stx2 + Stx2a | 0.8 | 0.8 | 0.97 | 0.67 | 1.05 |
| 97-8037 | Stx2 + Stx2a | 0.84 | 0.77 | 1.36 | 0.49 | 1.02 |
| 97-8075[c] | Stx2 + Stx2a | 1.12 | 0.8 | 0 | 0 | 0 |
| 95-0243 | Stx2b | 0.73 | 0.67 | 0.62 | 0 | 0 |
| 95-0459[c] | Stx2 + Stx2b | 0 | 0 | 0 | 0 | 0 |
| E32511 | Stx2c | 0.72 | 0.75 | 1.15 | 0 | 0 |
| pJH | Stx2c | 0.99 | 0.73 | 1.12 | 0 | 0 |

[a]Neutralization index is defined as the $\log_{10}$ of the dilution of Stx-containing culture supernatant neutralized by 1.25 μg/ml Stx2-specific Hu-mAb.
[b]On retyping, strains found to produce both Stx1 and Stx2; retyping experiments to be reconfirmed.
[c]On retyping, strains found to produce both Stx1 and Stx2; also preliminary evident of production of Stx2c.

TABLE 6

Summary of Stx1 Hu-mAb Isotype, Subunit Specificity, and in vivo and in vitro Neutralization of Stx1[a].

| mAb | Isotype[b] | Stx1 Subunit Specificity | HeLa Cell Cytotoxicity Assay (% Neutralization of Stx1 ± S.D.)[c] | Murine Survival[d] | |
|---|---|---|---|---|---|
| | | | | Average ± S.D. (Days) | p-value |
| 2D9 | IgM$_x$ | B | 100.0 ± 0 | 12.0 ± 0[e] | 0.00005 |
| 5A4 | IgG1$_k$ | B | 88.7 ± 1.15 | 12.0 ± 0[f] | 0.00005 |
| 10F4 | IgG1$_k$ | B | 99.7 ± 0.14 | 12.0 ± 0[e] | 0.00005 |
| 15G2 | IgG1$_k$ | B | 96.2 ± 1.59 | 12.0 ± 0[e] | 0.00005 |
| 15G9 | IgM$_k$ | B | 96.9 ± 5.03 | 12.0 ± 0[e] | 0.00005 |
| 1B10 | IgM$_k$ | B | 63.3 ± 18.46 | 9.55 ± 3.95[e] | 0.00071 |
| 7E12 | IgM$_k$ | A | 75.7 ± 9.29 | 9.08 ± 4.52[e] | 0.03389 |
| 8A5 | IgM$_k$ | B | 57.7 ± 10.26 | 5.39 ± 3.77[e] | 0.13821 |
| 13F1 | IgG1$_k$ | B | ND | ND | — |
| 14C9 | IgM$_k$ | B | 76.3 ± 13.35 | 6.80 ± 4.49[e] | 0.14342 |
| 14H3 | IgM$_k$ | B | 77.3 ± 5.91 | 7.95 ± 4.28[e] | 0.00268 |

[a]Stx1 Hu-mAbs have been sorted into two groups based on average percent neutralization of Stx1 in vitro and ability to prolong average in vivo. Upper group includes those Stx1 Hu-mAbs with in vitro percent neutralization values of >85% and average survival prolongation of >10 days. Lower group includes those Stx1 Hu-mAbs with in vitro percent neutralization values of <84% and average survival prolongation of <10 days. Although not tested in vitro or in vivo, Stx1 Hu-mAb 13F1 is listed in the lower group.
[b]All anti-Stx1 mAbs are comprised of human heavy and light chain isotypes as indicated with the exception of mAb 1E2 which is a hybrid comprised of a murine IgG2a heavy chain and a human kappa light chain.
[c]% Neutralization of 1 ng Stx1 in vitro in presence of 39.1 ng mAb
[d]Experiments were terminated on day 12; n = 6-10. Hu-mAbs which prolonged average survival >10 days are indicated in bold type. p-values were calculated for the comparison of average survival of PBS control groups and Hu-mAb treated groups by parametric (log-rank) and non-parametric (Wilcoxon) analyses. Comparable p-values were obtained with both analyses. The table shows p-values obtained by Wilcoxon analysis.
[e]Average survival of PBS control = 3.45 ± 0.64 days.
[f]Average survival of PBS control = 3.55 ± 0.93 days.

What is claimed is:

1. A dosage formulation comprising
    an effective amount of human or humanized monoclonal antibodies for intravenous administration to humans to produce a serum level of anti-Shiga toxin II antibodies of at least 0.5 micrograms/ml to prevent or treat systemic hemolytic uremic syndrome in a human,
    the antibodies consisting of antibodies having percent neutralization of Shiga-like toxin II in a HeLa cell cytotoxicity assay of greater than 70% and neutralizing Shiga-like toxin II in vivo,
    wherein the antibodies are specifically reactive with the alpha subunit of Shiga-like toxin II produced by *Escherichia coli* which causes hemolytic uremic syndrome in humans.

2. The dosage formulation of claim 1, wherein the antibodies are human monoclonal antibodies.

3. The dosage formulation of claim 1, wherein the antibodies are produced by recombinant DNA methodology.

4. The dosage formulation of claim 1, wherein the antibodies are chimeric monoclonal antibodies.

5. The dosage formulation of claim 1 wherein the antibodies are effective to prevent neurological signs of hemolytic uremic syndrome or lesions,
    wherein the neurological signs or lesions are selected from the group consisting of cerebral hemorrhaging and convulsions.

6. The dosage formulation of claim 1, wherein the antibodies are effective to prolong survival.

7. The dosage formulation of claim 1 equivalent to 4 ml serum from an animal immunized with Shiga-like toxin II/kg body weight.

8. The dosage formulation of claim 1 equivalent to a dosage of 3 mg human monoclonal antibody to Shiga-like toxin II administered to a newborn pig.

9. The dosage formulation of claim 1 having a percent neutralization of Shiga-like toxin II in a HeLa cell cytotoxity assay of between greater than 90%.

10. The dosage formulation of claim 1 wherein the antibodies are a human monoclonal antibody specifically reactive with the alpha subunit of the Shiga-like toxin II deposited on Dec. 12, 2001 with the American Type Culture Collection, ATCC Accession No. 5C12.

* * * * *

UNITED STATES PATENT AND TRADEMARK OFFICE
CERTIFICATE OF CORRECTION

| | | |
|---|---|---|
| PATENT NO. | : 7,910,706 B2 | Page 1 of 1 |
| APPLICATION NO. | : 11/855699 | |
| DATED | : March 22, 2011 | |
| INVENTOR(S) | : Saul Tzipori et al. | |

It is certified that error appears in the above-identified patent and that said Letters Patent is hereby corrected as shown below:

Specification, column 1, lines 15-20, replace
"STATEMENT REGARDING FEDERALLY SPONSORED RESEARCH
The U.S. government has certain right in this invention by virtue of grants from the National Institutes of Health AI41326 and DK 58993".
with
--GOVERNMENT SUPPORT
This invention was made with government support under grants AI041326 and DK058993 awarded by the National Institutes of Health. The government has certain rights in the invention--.

Claim 9, column 38, line 60, delete "between".

Signed and Sealed this
Twenty-seventh Day of September, 2011

David J. Kappos
*Director of the United States Patent and Trademark Office*